(12) United States Patent
Watanabe

(10) Patent No.: US 11,191,924 B2
(45) Date of Patent: Dec. 7, 2021

(54) CATHETER ASSEMBLY

(71) Applicant: TERUMO KABUSHIKI KAISHA, Tokyo (JP)

(72) Inventor: Kohei Watanabe, Fuji (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 174 days.

(21) Appl. No.: 16/507,087

(22) Filed: Jul. 10, 2019

(65) Prior Publication Data

US 2019/0329003 A1 Oct. 31, 2019

Related U.S. Application Data

(63) Continuation of application No. PCT/JP2018/012135, filed on Mar. 26, 2018.

(30) Foreign Application Priority Data

Mar. 29, 2017 (JP) .............................. JP2017-066373

(51) Int. Cl.
*A61M 25/01* (2006.01)
*A61M 25/00* (2006.01)
*A61M 25/09* (2006.01)

(52) U.S. Cl.
CPC .... *A61M 25/0133* (2013.01); *A61M 25/0097* (2013.01); *A61M 25/09041* (2013.01);
(Continued)

(58) Field of Classification Search
CPC .......... A61M 25/0133; A61M 25/0097; A61M 25/09041; A61M 25/0054; A61M 25/005;
(Continued)

(56) References Cited

U.S. PATENT DOCUMENTS 4,509,945 A * 4/1985 Kramann ........... A61M 25/0111
604/164.13
5,507,766 A 4/1996 Kugo et al.
(Continued)

FOREIGN PATENT DOCUMENTS

EP 0 608 853 A2 8/1994
GN 102371023 A 3/2012
(Continued)

OTHER PUBLICATIONS

An English Translation of the International Search Report (Form PCT/ISA/210) and the Written Opinion of the International Searching Authority (Form PCT/ISA/237) dated Jun. 5, 2018, by the Japanese Patent Office in corresponding International Application No. PCT/JP2018/012135. (7 pages).
(Continued)

*Primary Examiner* — Bhisma Mehta
*Assistant Examiner* — Neeraja Gollamudi
(74) *Attorney, Agent, or Firm* — Buchanan Ingersoll & Rooney PC

(57) ABSTRACT

A catheter assembly is disclosed, which includes a catheter, a catheter hub, a guide wire, and a guide wire hub. The guide wire has a guide wire rigidity changing portion that gradually decreases in rigidity from a proximal side toward a distal side, and the catheter has a catheter rigidity changing portion that gradually decreases in rigidity from a proximal side toward a distal side. In the catheter assembly, the catheter hub and the guide wire hub are connected to each other in a state where the distal side of the guide wire is exposed from a distal end of a lumen of a shaft portion and a guide wire rigidity changing point and a catheter rigidity changing point are aligned with each other in an axial direction.

20 Claims, 8 Drawing Sheets

(52) U.S. Cl.
CPC ............... *A61M 25/0054* (2013.01); *A61M 2025/09066* (2013.01); *A61M 2025/09133* (2013.01); *A61M 2025/09175* (2013.01)

(58) Field of Classification Search
CPC ........ A61M 25/09; A61M 2025/09066; A61M 2025/09133; A61M 2025/09175; A61M 2025/09166; A61M 25/008; A61M 25/0068; A61M 25/0009; A61M 25/0012; A61M 25/0013; A61M 25/141; A61M 25/0144; A61M 25/0169; A61M 25/0172
See application file for complete search history.

(56) References Cited

U.S. PATENT DOCUMENTS

| | | | |
|---|---|---|---|
| 5,865,767 A | | 2/1999 | Frechette et al. |
| 2009/0030400 A1* | | 1/2009 | Bose ................. A61M 25/0054 604/510 |
| 2010/0030165 A1* | | 2/2010 | Takagi ............... A61M 25/0054 604/265 |
| 2010/0174246 A1 | | 7/2010 | Bunch et al. |
| 2012/0041421 A1* | | 2/2012 | Nishigishi ............. A61M 25/09 604/528 |
| 2014/0212355 A1 | | 7/2014 | Trollsas et al. |
| 2014/0214005 A1* | | 7/2014 | Belson ............... A61M 25/0637 604/510 |
| 2016/0121081 A1* | | 5/2016 | Iwano ................ A61M 25/0026 604/96.01 |

FOREIGN PATENT DOCUMENTS

| | | |
|---|---|---|
| JP | 2002204831 A | 7/2002 |
| JP | 2012034922 A | 2/2012 |
| JP | 2016508486 A | 3/2016 |
| WO | 92/04861 A1 | 4/1992 |
| WO | 2008006111 A2 | 1/2008 |
| WO | 2014/124447 A1 | 8/2014 |

OTHER PUBLICATIONS

The extended European Search Report dated Dec. 18, 2020, by the European Patent Office in corresponding European Patent Application No. 18775096.3-1132. (5 pages).

International Search Report (PCT/ISA/210) dated Jun. 5, 2018, by the Japan Patent Office as the International Searching Authority for International Application No. PCT/JP2018/012135.

Written Opinion (PCT/ISA/237) dated Jun. 5, 2018, by the Japan Patent Office as the International Searching Authority for International Application No. PCT/JP2018/012135.

Office Action (Notification of the First Office Action) dated Feb. 2, 2021, by the National Intellectual Property Administration, PRC in corresponding Chinese Patent Application No. 201880013456.8 and an English Translation of the Office Action. (11 pages).

* cited by examiner

CATHETER ASSEMBLY

CROSS-REFERENCES TO RELATED APPLICATIONS

This application is a continuation of International Application No. PCT/JP2018/012135 filed on Mar. 26, 2018, which claims priority to Japanese Application No. 2017-066373 filed on Mar. 29, 2017, the entire content of both of which is incorporated herein by reference.

FIELD OF THE DISCLOSURE

The present disclosure relates to a catheter assembly.

BACKGROUND DISCUSSION

In the related art, a catheter device is used to perform a treatment or the like in a body lumen. A guide wire having a flexible core wire is used to guide the catheter device to a target site of the body lumen. For example, a transarterial chemoembolization (TACE) is a treatment method in which a catheter is advanced from an artery of the liver further to the vicinity of a tumor, and an anti-cancer agent or an embolic material is injected to selectively necrosis the tumor. In the TACE, a guide wire is used to advance the catheter.

In guiding the catheter to the target site, a procedure is performed, which includes advancing the catheter while following the guide wire that has been advanced. Furthermore, both the guide wire and the catheter can be advanced together using an integral structure type catheter assembly in which the guide wire is inserted into the catheter.

The integral structure type catheter assembly has a catheter hub attached to the proximal portion of the catheter, and a guide wire hub attached to the proximal portion of the guide wire and connected to the catheter hub in a freely detachable manner. Then, the catheter hub and the guide wire hub are connected to each other in a state where a predetermined range from the distal end of the guide wire is exposed from the distal end of the catheter.

A body lumen has an intricately curved or serpentine shape. In order to enhance operability when passing a guide wire into a body lumen, a guide wire can be provided with a rigidity changing portion that gradually decreases in rigidity from a proximal side toward a distal side (for example, see U.S. Pat. No. 5,865,767). The rigidity of the rigidity changing portion is changed by gradually decreasing a diameter of a core wire. Note that the "proximal side" means a side located on an opposite side, when a side introduced into the living body is referred to as a "distal side".

When a guide wire having a rigidity changing portion is applied to an integral structure type catheter assembly, simply connecting the guide wire and the catheter may cause an occurrence of discomfort in usability by an operator. For example, when the rigidity of the catheter is relatively large, the rigidity rapidly changes (increases) from the distal side to the proximal side, with the distal end of the catheter as a starting point where the guide wire is exposed as a boundary. Therefore, despite the use of a flexible guide wire, the operability of the integral structure type catheter assembly can be impeded.

SUMMARY

An integral structure type catheter assembly is disclosed, which includes a guide wire having a rigidity changing portion, which can suppress an occurrence of discomfort in usability and can improve the operability of the catheter assembly and the guide wire.

A catheter assembly according to the present disclosure can include a catheter that has a shaft portion having a lumen, a catheter hub that is attached to a proximal portion of the catheter, a guide wire that has a flexible core wire and is capable of being inserted into the lumen of the shaft portion, and a guide wire hub that is attached to a proximal portion of the guide wire and is freely detachably connected to the catheter hub. The guide wire has a guide wire rigidity changing portion that gradually decreases in rigidity from a proximal side toward a distal side. The catheter has a catheter rigidity changing portion that gradually decreases in rigidity from a proximal side toward a distal side. In the catheter assembly, the catheter hub and the guide wire hub are connected to each other in a state where the distal side of the guide wire is exposed from a distal end of the lumen of the shaft portion, and a guide wire rigidity changing point that is set in at least one place in the guide wire rigidity changing portion and a catheter rigidity changing point that is set in at least one place in the catheter rigidity changing portion are aligned with each other in an axial direction.

When a guide wire having a guide wire rigidity changing portion is applied to an integral structure type catheter assembly, a catheter hub and a guide wire hub are connected to each other, in a state where a catheter having a catheter rigidity changing portion is combined, and further, the guide wire rigidity changing point and the catheter rigidity changing point are aligned with each other in an axial direction. According to such a configuration, by changing a rigidity of the catheter in accordance with a rigidity change of the guide wire, it is possible to set a rigidity change in a desired pattern as a whole of integral structure type catheter assembly. Therefore, according to the present disclosure, an integral structure type catheter assembly can be provided to which a guide wire having a guide wire rigidity changing portion is applied, which can suppress an occurrence of discomfort in usability and can improve operability.

In accordance with an exemplary embodiment, a catheter assembly is disclosed comprising: a catheter having a shaft portion, the shaft portion having a lumen; a catheter hub configured to be attached to a proximal portion of the catheter; a guide wire having a flexible core wire, the guide wire configured to be inserted into the lumen of the shaft portion; a guide wire hub configured to be attached to a proximal portion of the guide wire and is freely detachably connected to the catheter hub; the guide wire having a guide wire rigidity changing portion that decreases in rigidity from a proximal side toward a distal side; the catheter having a catheter rigidity changing portion that decreases in rigidity from a proximal side toward a distal side; the catheter hub and the guide wire hub are connected to each other in a state where the distal side of the guide wire is exposed from a distal end of the lumen of the shaft portion; and wherein a guide wire rigidity changing point in the guide wire rigidity changing portion and a catheter rigidity changing point in the catheter rigidity changing portion are aligned with each other in an axial direction.

In accordance with another exemplary embodiment, a catheter assembly is disclosed comprising: a catheter having a shaft portion, the shaft portion having a lumen; a guide wire having a flexible core wire, the guide wire configured to be inserted into the lumen of the shaft portion; the guide wire having a guide wire rigidity changing portion that decreases in rigidity from a proximal side toward a distal side; the catheter having a catheter rigidity changing portion that decreases in rigidity from a proximal side toward a distal side; and wherein a guide wire rigidity changing point in the guide wire rigidity changing portion and a catheter rigidity changing point in the catheter rigidity changing portion are aligned with each other in an axial direction.

In accordance with an exemplary embodiment, a catheter assembly is disclosed comprising: a catheter having a shaft portion, the shaft portion having a lumen; a guide wire having a flexible core wire, the guide wire configured to be inserted into the lumen of the shaft portion; the guide wire having a guide wire rigidity changing portion that decreases in rigidity from a proximal side toward a distal side; the catheter having a catheter rigidity changing portion that decreases in rigidity from a proximal side toward a distal side; wherein a guide wire rigidity changing point in the guide wire rigidity changing portion and a catheter rigidity changing point in the catheter rigidity changing portion are aligned with each other in an axial direction; the core wire comprising: a distal core portion that includes a foremost distal end; a main body portion that constitutes a portion more proximal than the distal core portion and has a constant diameter along an axial direction; and the guide wire rigidity changing portion that constitutes a portion from a distal end of the main body portion to a proximal end of the distal core portion and decreases in rigidity from the main body portion toward the distal core portion, and wherein the guide wire rigidity changing portion includes at least: a first tapered portion that is continuous with the distal end of the main body portion and has a diameter decreasing from the main body portion toward the distal core portion; a second tapered portion that is continuous with a distal end of the first tapered portion and has a diameter decreasing from the first tapered portion toward the distal core portion; an n-th tapered portion that is continuous with the proximal end of the distal core portion and has a diameter decreasing from an (n−1)th tapered portion being continuous with the proximal side toward the distal core portion; and a gradient of a change in the diameter in the first tapered portion is larger than a gradient of a change in the diameter in the second tapered portion.

DETAILED DESCRIPTION

Figure 1A:
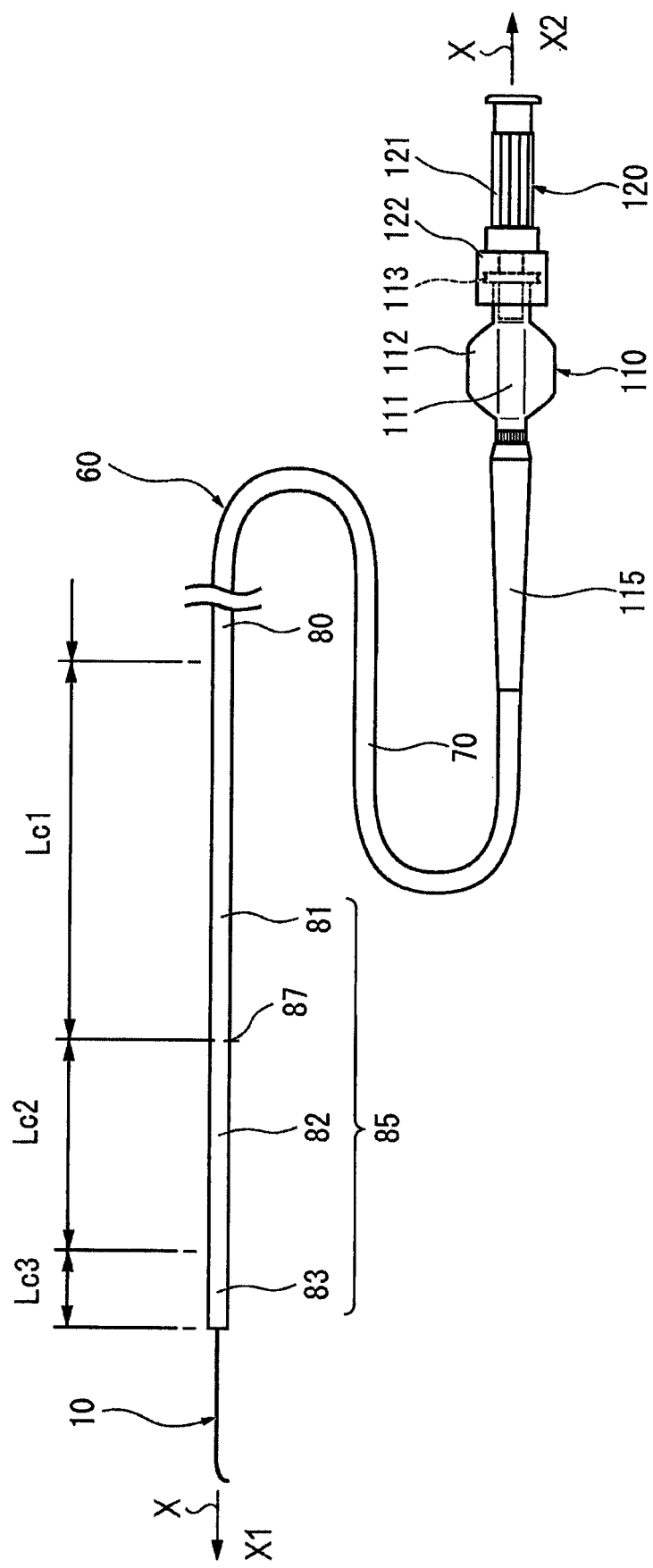
FIG. 1A is a schematic diagram showing an integral structure type catheter assembly.

Hereinafter, an embodiment of the present disclosure will be described with reference to the attached drawings. Note that the following description does not limit the technical scope or the meaning of terms described in the claims. Further, the dimensional ratios in the drawings are exaggerated for the sake of explanation, and may differ from the actual proportions.

Figure 1B:
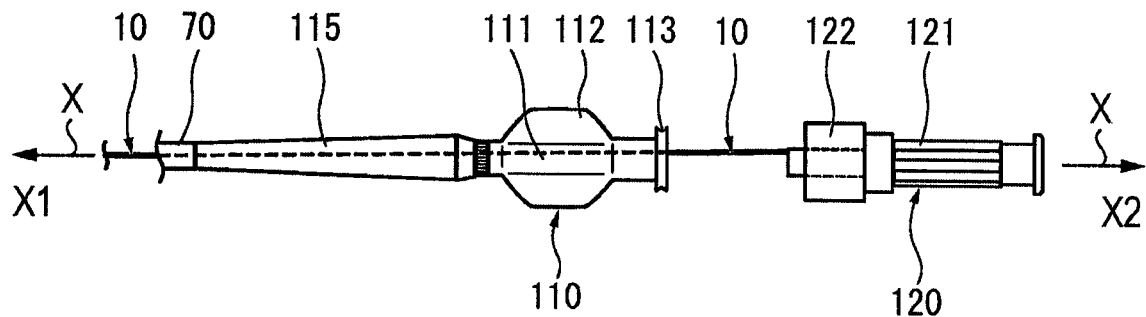
FIG. 1B is a schematic diagram showing the catheter assembly in a state where a connection between a catheter hub and a guide wire hub is released.
Figure 1C:
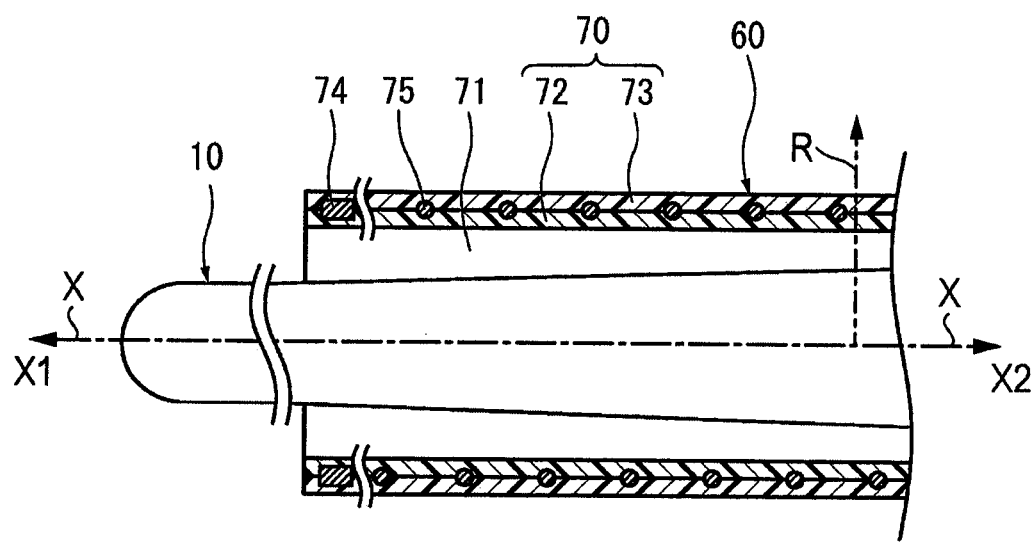
FIG. 1C is an axial direction cross-sectional diagram showing a distal part of the catheter assembly in an enlarged manner.
Figure 1D:
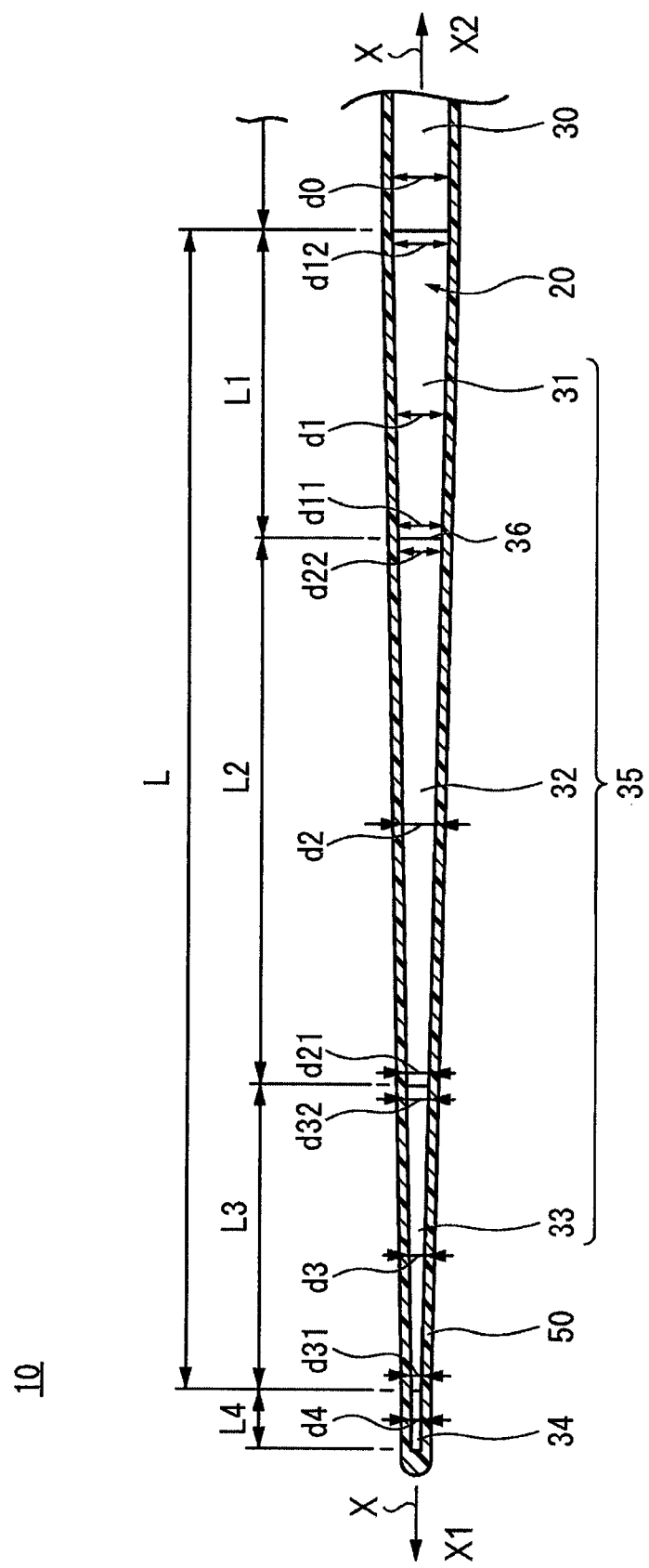
FIG. 1D is an axial direction cross-sectional diagram of a guide wire.
Figure 1E:
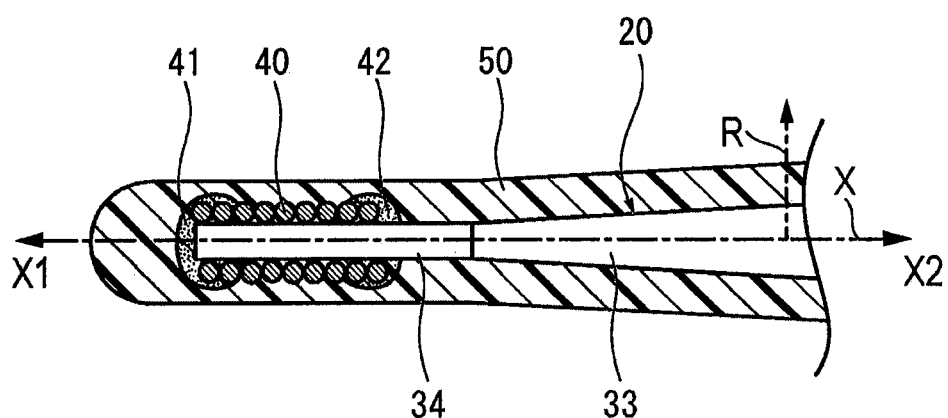
FIG. 1E is an axial direction cross-sectional diagram showing the distal part of the guide wire in an enlarged manner.
Figure 2:
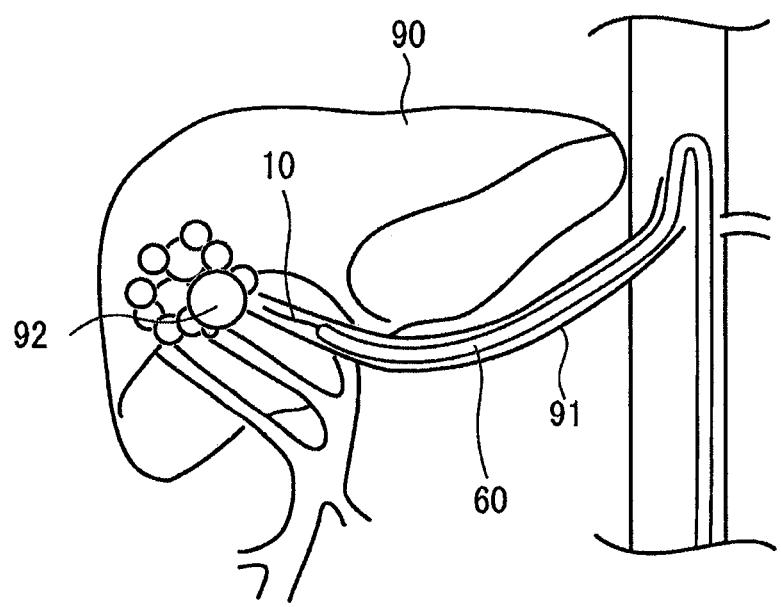
FIG. 2 is a diagram schematically showing an aspect in which an integral structure type catheter assembly is being advanced in a TACE.
Figure 3A:
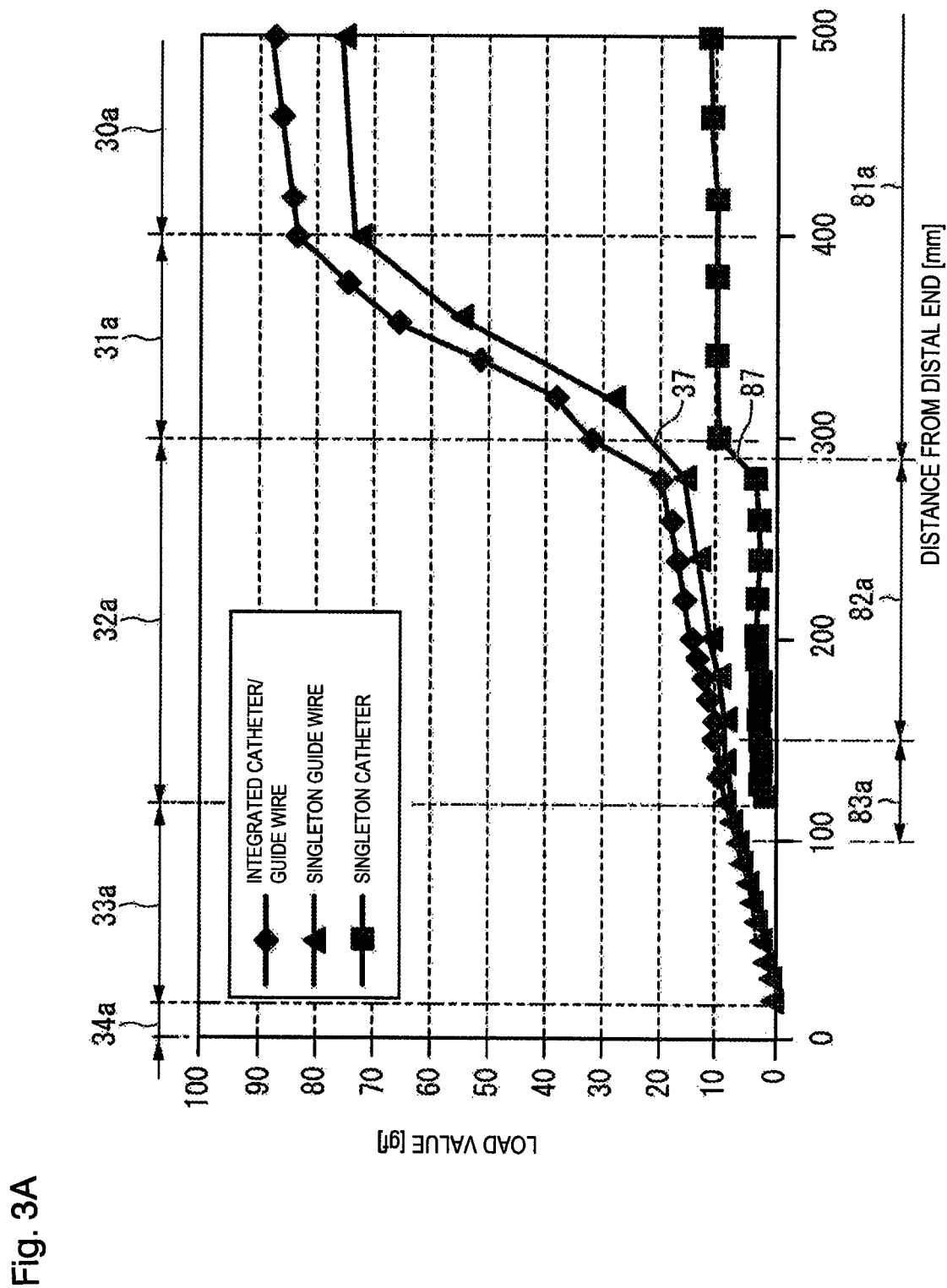
FIG. 3A is a graph showing flexural load values of each of singleton catheter, singleton guide wire, and the integral structure type catheter assembly, along an axial direction position of the guide wire.

FIG. 1A is a schematic diagram showing an integral structure type catheter assembly 100, FIG. 1B is a schematic diagram showing the catheter assembly 100 in a state in which a connection between a catheter hub 110 and a guide wire hub 120 is released, and FIG. 1C is an axial direction cross-sectional diagram showing a distal part of the catheter assembly 100 in an enlarged manner. FIG. 1D is an axial direction cross-sectional diagram of a guide wire 10, and FIG. 1E is an axial direction cross-sectional diagram showing a distal part of the guide wire 10 in an enlarged manner. FIG. 2 is a diagram schematically showing an aspect in which a catheter 60 is being advanced along the guide wire 10, for example, in the TACE. FIG. 3A is a graph showing flexural load values of each of singleton catheter 60, singleton guide wire 10, and the integral structure type catheter assembly 100, along an axial direction position of the guide wire 10.

In the description of the present specification, a long-length direction (left and right direction in FIG. 1A), in which a shaft portion 70 of the catheter 60 and the core wire 20 of the guide wire 10 extend, is defined as an axial direction, and is indicated by an arrow X in each drawing. A direction orthogonal to the axial direction is defined as a radial direction and is indicated by an arrow R in FIGS. 1C and 1E. In the catheter assembly 100, a side to be inserted into a living body (in the blood vessel) is defined as a distal side (distal side, left side in FIG. 1A) and is indicated by an arrow X1 in each drawing, and a side to be operated at the hand positioned opposite to the distal side is defined as a proximal side (proximal side, right side in FIG. 1A) and is indicated by an arrow X2 in each drawing. In the present specification, a distal portion means a part including a certain range in the axial direction from the distal end (the foremost distal end), and a proximal portion means a part including a certain range in the axial direction from the proximal end (the foremost proximal end).

In accordance with an exemplary embodiment, the catheter assembly 100 is disclosed with reference to FIGS. 1A to 1E, and 3A. The catheter assembly 100 has a catheter 60 having a shaft portion 70 with a lumen 71, a catheter hub 110 attached to a proximal portion of the catheter 60, the guide wire 10 having a flexible core wire 20 and which can be inserted into the lumen 71 of the shaft portion 70, and a guide wire hub 120 attached to the proximal portion of the guide wire 10 and connected to the catheter hub 110 in a freely detachable manner. In the catheter assembly 100, the guide wire 10 is inserted into the lumen 71 (guide wire lumen) of the therapeutic or diagnostic catheter 60. In accordance with an exemplary embodiment, the guide wire 10 has a guide wire rigidity changing portion 35 that gradually decreases in rigidity from the proximal side toward the distal side, and at least one guide wire rigidity changing point 37. The catheter 60 has a catheter rigidity changing portion 85 that gradually decreases in rigidity from the proximal side toward the distal side, and at least one catheter rigidity changing point 87. Then, in the catheter assembly 100, the catheter hub 110 and the guide wire hub 120 are connected to each other in a state where the distal side of the guide wire 10 is exposed from a distal end of the lumen 71 of the shaft portion 70, and the guide wire rigidity changing point 37 and the catheter rigidity changing point 87 are aligned with each other in the axial direction.

In the present specification, "a state in which the guide wire rigidity changing point 37 and the catheter rigidity changing point 87 are aligned with each other in the axial direction" is limited to a case where both the rigidity changing points 37 and 87 overlap at physically the same position. In a case of using as an integral structure type catheter assembly 100, both the rigidity changing points 37 and 87 are substantially aligned with each other in the axial direction within a range where an occurrence of discomfort in usability can be suppressed and operability can be improved. If both the rigidity changing points 37 and 87 are included in the range of a threshold value (for example, 20 mm), it can be regarded as "a state in which the guide wire rigidity changing point 37 and the catheter rigidity changing point 87 are aligned with each other in the axial direction". The threshold value is not uniquely determined, and also varies depending on the flexibility of the guide wire 10 and the catheter 60 and conditions such as the position and thickness of the blood vessel to be treated.

The integral structure type catheter assembly 100 is inserted into a body lumen and used to guide both the guide wire 10 and the catheter 60 together to a target site in the body lumen.

For example, as shown in FIG. 2, the transarterial chemoembolization (TACE) is a treatment method in which the catheter 60 is advanced from an artery 91 of the liver 90 further to the vicinity of a tumor 92, and an anti-cancer agent or an embolic material is injected to selectively necrosis the tumor. In the TACE, an integral structure type catheter assembly 100 can be used.

A body lumen has an intricately curved or serpentine shape. Therefore, when the catheter assembly 100 passes through the body lumen, a large bending load acts on the catheter assembly 100 as the distal portion of the catheter assembly 100 reaches the deep side (i.e., relatively large distance) of the body lumen.

Hereinafter, the configuration of each portion will be described in detail.

Catheter 60

In accordance with an exemplary embodiment, the catheter 60 has a substantially circular cross section, and has an elongated shaft portion 70 which can be introduced into a living body, and the catheter hub 110 is connected to a proximal portion of the shaft portion 70. The catheter 60 has a kink resistant protector (strain relief) 115 near a connection portion between the shaft portion 70 and the catheter hub 110. Note that the catheter 60 is not limited to the form in FIG. 1A, and, for example, may not have the kink resistant protector 115.

As shown in FIG. 1C, the shaft portion 70 is configured as a tubular shaped member having flexibility in which a lumen 71 extending in the axial direction is formed. The length of the shaft portion 70 can be, for example, about 700 mm to about 2000 mm, and preferably about 1000 mm to about 1500 mm although the preferable value varies depending on conditions such as the position and thickness of the blood vessel to be treated. The outer diameter (thickness) of the shaft portion 70 can be, for example, about 0.4 mm to about 3.0 mm, and preferably about 0.5 mm to about 1.1 mm although the preferable value varies depending on conditions such as the position and thickness of the blood vessel to be treated. The inner diameter of the shaft portion 70 (the outer diameter of the lumen 71) can be, for example, about 0.3 mm to about 2.3 mm, and preferably about 0.4 mm to about 0.8 mm although the preferable value varies depending on the thickness of the guide wire 10 to be inserted and conditions such as the position and thickness of the blood vessel to be treated.

In accordance with an exemplary embodiments, as shown in FIG. 1C, the shaft portion 70 has a tubular shaped inner layer 72, and an outer layer 73 is configured to cover an outer surface of the inner layer 72. At a part of the distal portion of the shaft portion 70, a contrast portion 74 formed of a material having radiopacity is disposed (or located) between the inner layer 72 and the outer layer 73. Note that a distal end tip for adding flexibility may be provided at the distal end of the shaft portion 70. The shaft portion 70 is provided with a reinforcement body 75 formed by braiding a wire at a site more proximal than the site where the contrast portion 74 is formed.

In accordance with an exemplary embodiment, the inner layer 72 of the shaft portion 70 is formed of a material softer than the guide wire 10 described later. For example, the inner layer 72 material can be a resin such as a fluorine-containing ethylenic polymer such as a polytetrafluoroethylene (PTFE), a tetrafluoroethylene-perfluoroalkyl vinyl ether copolymer (PFA), a tetrafluoroethylene-hexafluoropropylene copolymer (FEP), an ethylene-tetrafluoroethylene copolymer (ETFE), or a polyamide such as a nylon, or a polyamide elastomer such as a nylon elastomer can be used. Among the above, polytetrafluoroethylene (PTFE) or tetrafluoroethylene-perfluoroalkyl vinyl ether copolymer (PFA) having high lubricity can be suitably used. By using these materials, the frictional resistance of the inner surface of the shaft portion 70 can be reduced, so that the operability of the guide wire 10 inserted into the lumen 71 of the shaft portion 70 when the catheter 60 is used, can be improved.

In accordance with an exemplary embodiment, the outer layer 73 material can be, for example, a polymeric material such as a polyolefin (for example, a polyethylene, a polypropylene, a polybutene, an ethylene-propylene copolymer, an ethylene-vinyl acetate copolymer, an ionomer, or a mixture of two or more thereof, or the like), a polyvinyl chloride, a polyamide, a polyester, a polyester elastomer, a polyamide elastomer, a polyurethane, a polyurethane elastomer, a polyimide, a fluorocarbon resin, or a mixture thereof can be mentioned. The outer layer 73 may have a multilayer structure formed by laminating different resin materials. In addition, it is also possible to form a hydrophilic coating layer or the like by coating the outer surface of the outer layer 73 with a material made of a hydrophilic polymer.

In accordance with an exemplary embodiment, the contrast portion 74 is made of a metal material or resin material having a higher radiopacity than the inner layer 72 and the outer layer 73. The metal material of the contrast portion 74 having radiopacity can be made of, for example, a platinum, a gold, a silver, a tungsten or an alloy platinum, gold, silver, or tungsten. The resin material of the contrast portion 74 having radiopacity can be formed by coating or containing an X-ray contrast substance on the resin material or the like not having radiopacity. As the X-ray contrast substance, a powdered inorganic material, for example, such as tungsten, a barium sulfate, and a bismuth oxide may be used.

In accordance with an exemplary embodiment, the catheter hub 110 can be fluid-tightly attached to the proximal portion of the shaft portion 70 by an adhesive or a fixing tool (not shown). The catheter hub 110 has a main body portion 111 having a lumen and a pair of handle portions 112 protruding on a side portion of the main body portion 111. The catheter hub 110 functions as an insertion port of the guide wire 10 to the lumen 71 of the shaft portion 70 and an inlet port, for example, for a contrast agent, a drug solution, an embolic material or the like. The catheter hub 110 functions as a grip portion when operating the catheter 60. At the proximal portion of the main body 111, an external thread portion 113 is formed.

In accordance with an exemplary embodiment, the material of the catheter hub 110 can be, for example, a synthetic resin such as a polycarbonate, a polyolefin, a styrene resin, a polyamide, a polyester, or a stainless steel, or an aluminum, or an aluminum alloy. The polyolefin used for the catheter hub 110 can be, for example, a polyethylene, a polypropylene, an ethylene-propylene copolymer.

The kink resistant protector 115 can be made of an elastic material provided so as to surround a part of the proximal portion of the shaft portion 70. t The material of the kink resistant protector 115 can be, for example, a natural rubber, a silicone resin, or the like.

In accordance with an exemplary embodiment, the catheter 60 has a catheter rigidity changing portion 85 that gradually decreases in rigidity from the proximal side toward the distal side of the catheter 60. In accordance with an exemplary embodiment, the catheter rigidity changing portion 85 can be set with at least one catheter rigidity changing point 87.

In the present embodiment, the catheter rigidity changing portion 85 gradually decreases the rigidity of the shaft portion 70 of the catheter 60 from the proximal side toward the distal side of the shaft portion 70 of the catheter 60. As shown in FIG. 1A, the catheter rigidity changing portion 85 is divided into three regions, which includes a first region 81, a second region 82, and a third region 83 in order from the proximal side toward the distal side of the shaft portion 70. In accordance with an exemplary embodiment, a base region 80 continuous with a proximal end of the first region 81 has a constant rigidity along the axial direction.

In FIG. 3A, the first region 81 is indicated by the reference numeral 81a, the second region 82 is indicated by the reference numeral 82a, and the third region 83 is indicated by the reference numeral 83a.

In accordance with an exemplary embodiment, the catheter rigidity changing portion 85 can be configured, for example, by arranging a plurality of materials with different hardness along the axial direction. In the present embodiment, the outer layer 73 of the shaft portion 70 has a plurality of regions having different hardness along the axial direction, and the hardness of the material constituting each region decreases toward the distal side (flexibility increases towards the distal side) of the shaft portion 70. The hardness of the material constituting the outer layer 73 in the third region 83 is lower than the hardness of the material constituting the outer layer 73 in the second region 82. The hardness of the material constituting the outer layer 73 in the second region 82 is lower than the hardness of the material constituting the outer layer 73 in the first region 81. The hardness of the material constituting the outer layer 73 in the first region 81 is lower than the hardness of the material constituting the outer layer 73 in the base region 80. Accordingly, in the shaft portion 70 of the catheter 60, the third region 83 is configured to be more flexible than the second region 82, the second region 82 is configured to be more flexible than the first region 81, and the first region 81 is configured to be more flexible than the base region 80.

An example of the hardness of the material of the outer layer 73 of the catheter shaft 70 in the base region 80, in the first region 81, the second region 82, and the third region 83 will be further described below. In accordance with an exemplary embodiment, the hardness is a value measured by a type D durometer in accordance with ASTM D2240. In accordance with an exemplary embodiment, the third region 83 is the most flexible because it is positioned on the most distal side of the catheter, and the hardness of its constituent material is preferably, for example, 20 D to 40 D, and more preferably 25 D to 35 D. The second region 82 is flexible next to the third region 83, and the hardness of its constituent material is preferably, for example, 25 D to 60 D, and more preferably 30 D to 40 D. In accordance with an exemplary embodiment, the first region 81 has a suitable hardness to transmit the operation of the operator from the proximal side to the distal side, and the hardness of its constituent material is preferably, for example, 40 D to 80 D, and more preferably 60 D to 70 D. The base region 80 has a sufficient hardness for an operator to operate directly, and the hardness of its constituent material is preferably, for example, 50 D to 90 D, and more preferably 70 D to 80 D.

In accordance with an exemplary embodiment, in order to realize the hardness as set forth above, the above-mentioned constituent materials are used for the outer layer 73, and, for example, a plurality of different materials may be combined. Further, in order to adjust the hardness to an optimum range, additives may be added to the constituent materials. The thickness of the outer layer 73 can also be changed for the purpose of adjusting the hardness.

In accordance with an exemplary embodiment, the preferred value of the axial length of each region in the catheter rigidity changing portion 85 varies depending on the aspect (the number of regions, the axial length of each region, or the like) of the guide wire rigidity changing portion 35 in the guide wire 10 inserted and connected to the catheter 60. The preferred value of the axial length of each region in the catheter rigidity changing portion 85 also varies depending on the dimension by which the distal side of the guide wire 10 is exposed from the distal end of the shaft portion 70. For example, the axial length Lc1 of the first region 81 can be, for example, 250 mm, the axial length Lc2 of the second region 82 can be, for example, 140 mm, and the axial length Lc3 of the third region 83 can be, for example, 50 mm. In accordance with an exemplary embodiment, the axial length of the base region 80 can vary depending on the product length. In accordance with an exemplary embodiment, the exposed length of the distal side of the guide wire 10 can be, for example, 100 mm.

In accordance with an exemplary embodiment, the thickness of the inner layer 72 in the shaft portion 70 can be constant over the entire length in the axial direction.

In the catheter 60 of the present embodiment, the rigidity changes at three points, the first change between the third region 83 and the second region 82, the second change between the second region 82 and the first region 81, and the third change between the first region 81 and the base region 80. As shown in FIG. 3A, the change in rigidity between the second region 82 and the first region 81 is the largest. Thus, in the present embodiment, the catheter rigidity changing point 87 is set between the second region 82 and the first region 81 (see reference numeral 87 in FIG. 3A).

With the catheter rigidity changing point 87 as a boundary, the rigidity on the distal side is smaller than the rigidity on the proximal side, and the material forming the proximal side of the shaft portion 70 and the material forming the distal side of the shaft portion 70 are different. Note that in accordance with an exemplary embodiment, "a material is different" includes both cases when the polymer itself is different and when the polymer itself is the same but the grade is different.

The flexural load values of each of the singleton catheter 60, the singleton guide wire 10, and the integral structure type catheter assembly 100 will be described later.

Guide Wire 10

Referring to FIGS. 1D and 1E, the guide wire 10 has an extending core wire 20 in the axial direction and a guide wire hub 120 connected to the proximal portion of the core wire 20. The guide wire 10 has a marker portion 40 disposed at the distal portion of the core wire 20 and a coating layer 50 coating the core wire 20.

The length of the guide wire 10 is, although the preferable value varies depending on the position, thickness or the like of the blood vessel to be applied, preferably 500 mm to 4000 mm, for example. The outer diameter (thickness) of the main body portion 30 can be, although the preferable value varies depending on the position, thickness or the like of the blood vessel to be applied, preferably 0.15 mm to 2.0 mm, for example.

The material from which the core wire 20 is fabricated is not limited as long as it has flexibility, and, for example, the material of the core wire 20 can be a metal such as a stainless steel (SUS), a spring steel, titanium, tungsten, tantalum, and a super-elastic alloy such as a nickel-titanium alloy, and a hard plastic such as a polyimide, a polyamide, a polyester, a polycarbonate, and a glass fiber, and combination of metals, super-elastic alloys, hard plastics, and glass fibers.

As shown in FIG. 1B, the proximal portion of the guide wire 10 is attached to a wall portion of the distal portion of the guide wire hub 120. The guide wire hub 120 has a main body portion 121 having a lumen, and a ring portion 122 disposed on the distal side of the main body portion 121. When an injection molding is performed on the main body portion 121, the proximal portion of the guide wire 10 is inserted. The guide wire hub 120 is used in connection with the catheter hub 110 and functions as an inlet port, for example, for a liquid such as a contrast agent into the lumen 71 of the shaft portion 70. The liquid can be injected or withdrawn while the guide wire 10 is inserted into the lumen 71 of the shaft portion 70. In the ring portion 122, the internal thread (not shown) to be screwed into the external thread 113 of the catheter hub 110 is formed on an inner peripheral surface. The ring portion 122 can rotate with respect to the main body portion 121, and by engaging with a convex portion (not shown) formed on the outer periphery of the main body portion 121, the ring portion 122 is restricted from coming out of the main body portion 121 in the distal end direction.

As shown in FIG. 1A, the distal portion of the guide wire hub 120 is fitted into the lumen of the catheter hub 110, and the ring portion 122 is rotated to screw the external thread 113 and the internal thread and tighten with a certain amount of torque. As a result, the catheter hub 110 and the guide wire hub 120 can be fluid-tightly connected, and this connection state between the catheter hub 110 and the guide wire hub 120 can be maintained. The external thread portion 113 and the ring portion 122 having an internal thread portion constitute a lock means for fixing the connection state of the catheter hub 110 and the guide wire hub 120.

The material of the guide wire hub 120 can be, for example, a synthetic resin such as a polycarbonate, a polyolefin, a styrene resin, a polyamide, a polyester. The polyolefin can be, for example, a polyethylene, a polypropylene, an ethylene-propylene copolymer.

Referring to FIG. 1E, a marker portion 40 is disposed to cover the distal core portion 34 in a certain range extending in the axial direction. In accordance with an exemplary embodiment, the marker portion 40 can be a wire wound in a spiral shape around the distal core portion 34. The distal portion of the marker portion 40 is fixed near the distal portion of the distal core portion 34 through a fixing material 41. The proximal portion of the marker portion 40 is fixed near the proximal portion of the distal core portion 34 through a fixing material 42. The fixing materials 41 and 42 can be made of, for example, various adhesives, solder, or the like.

In accordance with an exemplary embodiment, the marker portion 40 is made of a material having radiopacity (radiopaque property). Examples of materials of the marker portion 40 having the radiopacity can include metal materials such as noble metals such as gold, platinum, tungsten or alloys containing noble metals (for example, platinum-iridium alloy). By providing the marker portion 40 in the distal core portion 34, the guide wire 10 can be inserted into a living body while confirming the position of the distal portion of the guide wire 10 under radioscopy.

In accordance with an exemplary embodiment, the coating layer 50 can be made of a resin material and formed to cover the entire core wire 20 including the marker portion 40. The distal portion of the coating layer 50 is preferably a rounded shape so as not to damage the inner wall of the body lumen.

In accordance with an exemplary embodiment, the coating layer 50 is preferably made of a material that can reduce friction. Thereby, the frictional resistance (sliding resistance) with the catheter 60 through which the guide wire 10 is inserted or the body lumen can be reduced and the sliding performance can be improved, and the operability of the guide wire 10 can be improved. Further, since the sliding resistance of the guide wire 10 is reduced, it is possible to more reliably prevent kinks (bend) or twists of the guide wire 10.

In accordance with an exemplary embodiment, the resin material constituting the coating layer 50 is preferably a material having relatively high flexibility, for example, polyolefin such as polyethylene and polypropylene, polyvinyl chloride, polyester (PET, PBT, or the like), polyamide, polyimide, polyurethane, polystyrene, polycarbonate, silicone resins, fluorine-based resins (PTFE, ETFE, PFA, or the like), composite materials thereof, various rubber materials such as latex rubber and silicone rubber, or composite materials obtained by combining two or more in these which is mentioned above. Among the above materials for the coating layer 50, it is more preferable to use a urethane resin from the viewpoint of further improving the flexibility. As a result, the distal portion of the guide wire 10 can be made flexible, so that it is possible to prevent the inner wall of the body lumen from being damaged when inserting the guide wire 10 into the body lumen.

In accordance with an exemplary embodiment, the thickness of the coating layer 50 is not particularly limited, and is preferably, for example, 5 μm to 500 μm. Note that the coating layer 50 is not limited to a single layer structure, and may be configured by laminating a plurality of layers.

In accordance with an exemplary embodiment, the coating layer 50 is preferably covered with a hydrophilic coating layer not shown. Since the sliding performance is improved by being covered by the hydrophilic coating layer, the guide wire 10 can be further prevented from being caught on the inner wall of the body lumen or the catheter 60.

The constituent material of the hydrophilic coating layer is not particularly limited, and for example, hydrophilic substances may be used, such as a cellulose-based polymer substance, polyethylene oxide polymer substance, maleic anhydride-based polymer substance (for example, maleic anhydride copolymer such as methyl vinyl ether-maleic anhydride copolymer), acrylamide-based polymer substance (for example, block copolymers of polyacrylamide, polyglycidyl methacrylate-dimethyl acrylamide (PGMA-DMAA)), water soluble nylon, polyvinyl alcohol, and polyvinyl pyrrolidone.

The thickness of the hydrophilic coating layer is not particularly limited, and is preferably, for example, 0.1 µm to 100 µm.

In accordance with an exemplary embodiment, the guide wire 10 has a guide wire rigidity changing portion 35 that gradually decreases in rigidity from the proximal side toward the distal side. In accordance with an exemplary embodiment, the guide wire rigidity changing portion 35 can be set with at least one guide wire rigidity changing point 37.

In the present embodiment, the guide wire rigidity changing portion 35 gradually decreases the rigidity of the core wire 20 from the proximal side to the distal side. As shown in FIG. 1D, the guide wire rigidity changing portion 35 can be divided into three regions of a first region 31, a second region 32, and a third region 33 in order from the proximal side to the distal side of the core wire 20. A base region 30 continuous with a proximal end of the first region 31 has a constant rigidity along the axial direction.

In accordance with an exemplary embodiment, the guide wire rigidity changing portion 35 can be configured, for example, by making the diameter of the core wire 20 different along the axial direction. In the present embodiment, the core wire 20 has a plurality of regions with different tapered angles, and the diameter of the core wire 20 decreases toward the distal side (flexibility increases toward the distal side). The first region 31, the second region 32, the third region 33, and the base region 30 will be referred to as a first tapered portion 31, a second tapered portion 32, a third tapered portion 33, and a main body portion 30, respectively. The distal side diameter of the third tapered portion 33 is smaller than the distal side diameter of the second tapered portion 32. The distal side diameter of the second tapered portion 32 is smaller than the distal side diameter of the first tapered portion 31. The distal side diameter of the first tapered portion 31 is smaller than the distal side diameter of the main body portion 30. As a result, in the core wire 20, the third tapered portion 33 is configured to be more flexible than the second tapered portion 32, the second tapered portion 32 is configured to be more flexible than the first tapered portion 31, and the first tapered portion 31 is configured more flexible than the main body portion 30. Hereinafter, the change in a diameter dimension of the core wire 20 will be further described.

With regard to a diameter of the core wire 20, as shown, for example, in FIG. 1D, numbers (1, 2, 3) of the suffix "x" represented as a diameter dxy represent a first tapered portion 31, a second tapered portion 32, and a third tapered portion 33, respectively. The numbers (1, 2) of the suffix "y" represent the distal side and the proximal side, respectively. With regard to a flexural load value of the core wire 20, numbers (1, 2, 3) of the suffix "x" represented as a flexural load value fxy represent the first tapered portion 31, the second tapered portion 32, and the third tapered portion 33, respectively. The numbers (1, 2) of the suffix "y" represent the distal side and the proximal side, respectively.

Figure 3B:
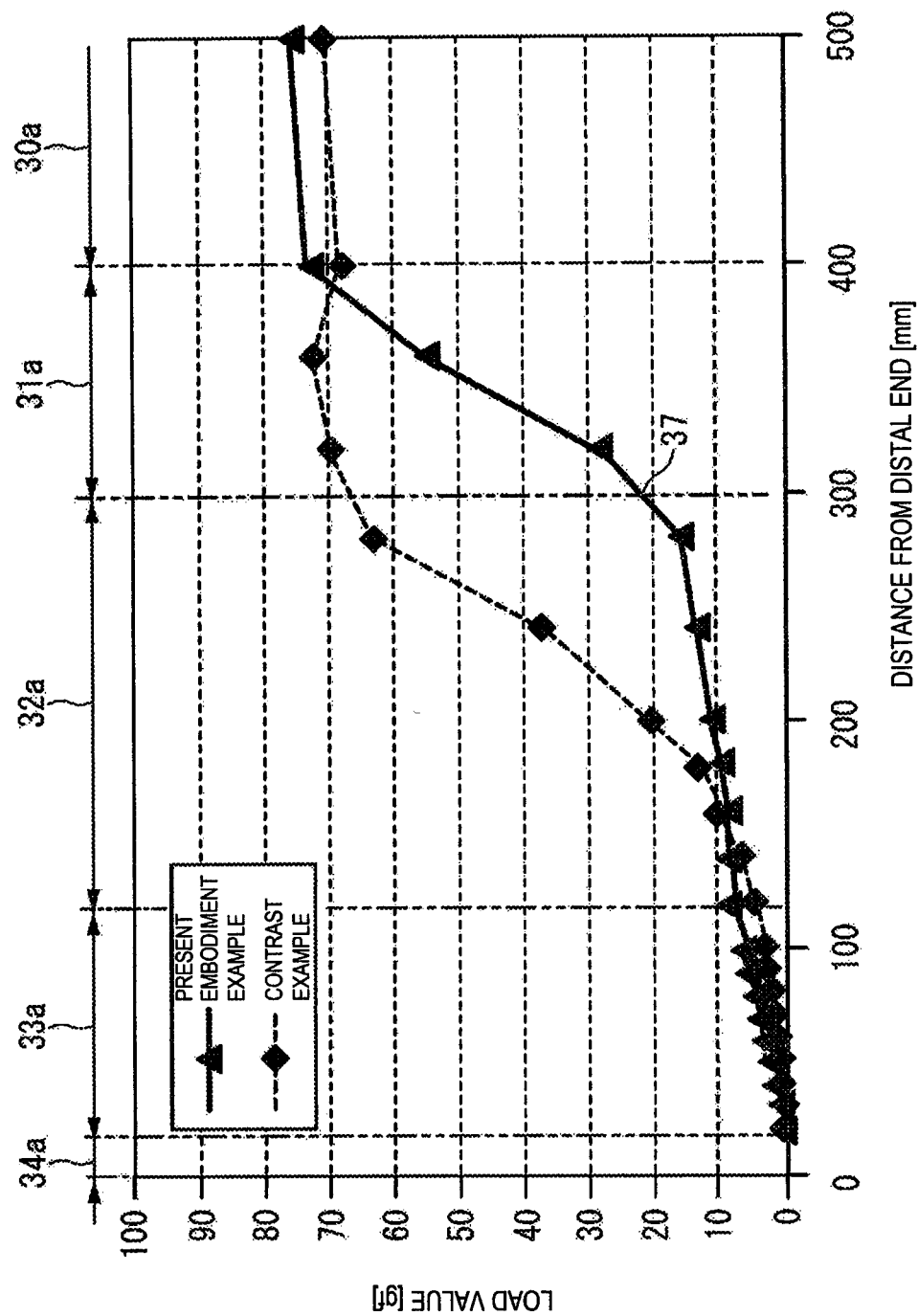
FIG. 3B is a graph showing flexural load values of the core wire of the guide wire along an axial position of the core wire.
Figure 3C:
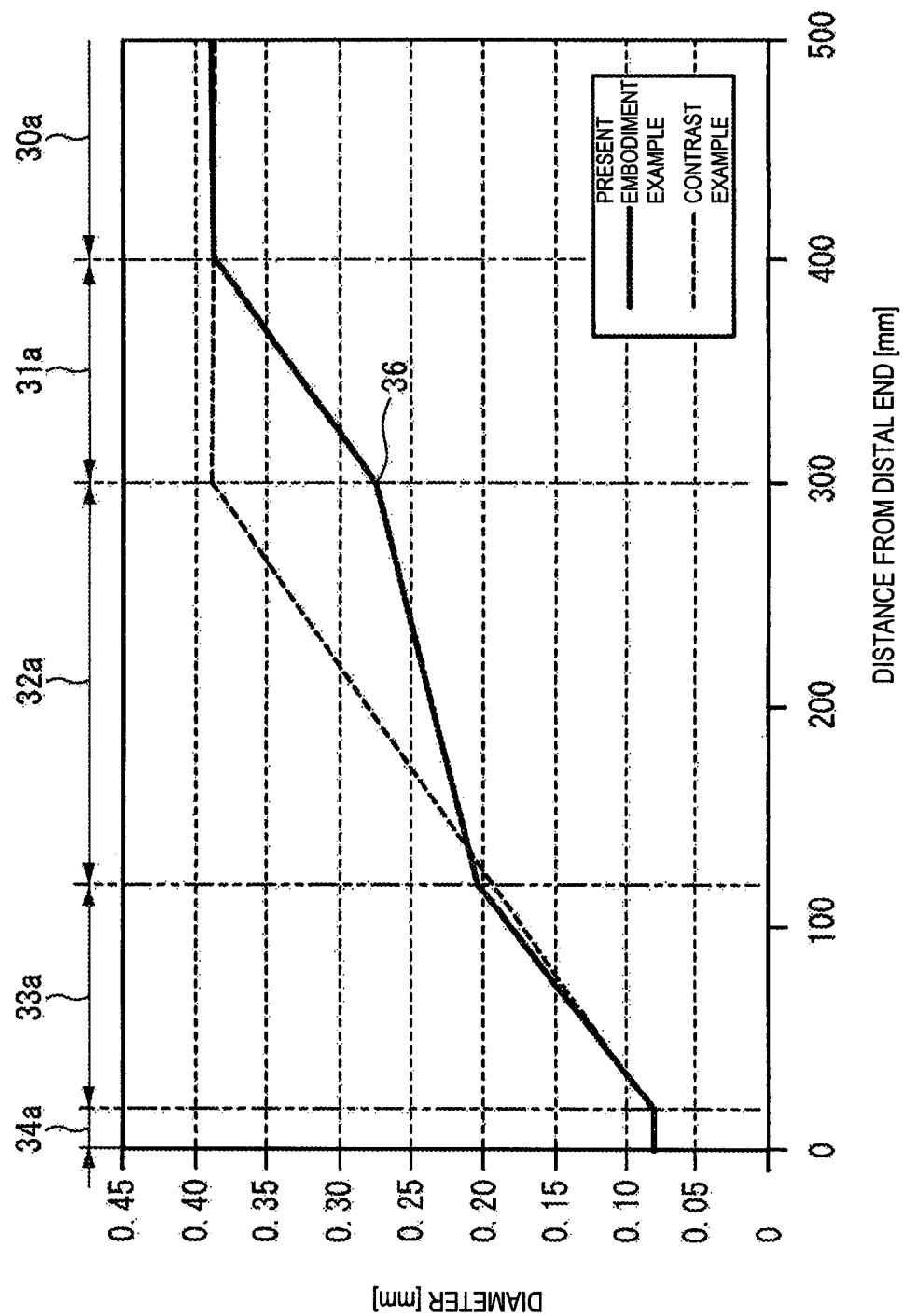
FIG. 3C is a graph showing diameters of the core wire of the guide wire along the axial position of the core wire.

FIG. 3B is a graph showing flexural load values of the core wire 20 of the guide wire 10 along the axial direction position of the core wire 20, and FIG. 3C is a graph showing diameters of the core wire 20 of the guide wire 10 along the axial direction position of the core wire 20. Note that the coating layer 50 coating the core wire 20 does not actually contribute to the rigidity of the guide wire 10. Therefore, the rigidity of the core wire 20 can be regarded as the rigidity of the guide wire 10, and the guide wire rigidity changing portion 35 also indicates the rigidity changing portion of the core wire 20.

As shown in FIGS. 1D and 1E, the core wire 20 has a flexibility, and has the distal core portion 34, the main body portion 30, and the guide wire rigidity changing portion 35. Including a foremost distal end, the distal core portion 34 is the most flexible site in the entire length of the core wire 20. The main body portion 30 constitutes a portion more proximal than the distal core portion 34 and is a site having a constant diameter d0 along the axial direction. The guide wire rigidity changing portion 35 constitutes a portion from the distal end of the main body portion 30 to the proximal end of the distal core portion 34, and is a site that gradually decreases in rigidity from the main body portion 30 toward the distal core portion 34.

In accordance with an exemplary embodiment, the guide wire rigidity changing portion 35 includes at least the first tapered portion 31, the second tapered portion 32, . . . , the (n−1)th tapered portion, and the n-th tapered portion 33 (where, n≥3), in order from the proximal side to the distal side. Each of the tapered portions 31, 32, . . . , 33 has a tapered shape that gradually decreases in diameter (inclined to the axial direction). In the illustrated embodiment, the guide wire rigidity changing portion 35 includes three tapered portions (n=3). Therefore, the second tapered portion 32 corresponds to the (n−1)th tapered portion. The n-th tapered portion 33 is hereinafter referred to as a "third tapered portion 33".

In FIGS. 3A, 3B, and 3C, a region of the distal core portion 34 is indicated by a reference numeral 34a, and a region of the main body portion 30 is indicated by a reference numeral 30a. Further, a region of the first tapered portion 31 is indicated by a reference numeral 31a, a region of the second tapered portion 32 is indicated by a reference numeral 32a, and a region of the third tapered portion 33 is indicated by a reference numeral 33a.

In the present exemplary embodiment, the core wire 20 is formed of a single material. The diameter of the core wire 20 varies along the axial direction. Thereby, the rigidity of the core wire 20 changes along the axial direction.

In accordance with an exemplary embodiment, the main body portion 30 has a constant diameter d0 along the axial direction. The distal core portion 34 also has a constant diameter d4 along the axial direction.

In the present specification, "having a constant diameter along the axial direction" does not mean to be limited to a case of physically having the same diameter. In a range in which the rigidity (flexural rigidity or torsional rigidity) of the main body portion 30 or the distal core portion 34 can be made substantially constant, it is sufficient to have a substantially constant outer diameter dimension.

In accordance with an exemplary embodiment, the first tapered portion 31 is continuous with the distal end of the main body portion 30 and has a diameter d1 that gradually decreases from the main body portion 30 toward the distal core portion 34. The second tapered portion 32 is continuous with the distal end of the first tapered portion 31 and has a diameter d2 that gradually decreases from the first tapered portion 31 toward the distal core portion 34. The third tapered portion 33 is continuous with the proximal end of the distal core portion 34, and has a diameter d3 that gradually decreases from the second tapered portion 32 continuous with the proximal side, toward the distal core portion 34.

In accordance with an exemplary embodiment, the boundary portion 36 between the first tapered portion 31 and the second tapered portion 32 is preferably located within a range of, for example, 300 mm to 400 mm from the foremost distal end of the distal core portion 34. Furthermore, it is preferable that the gradient $((d12-d11)/L1)$ of the change in the diameter d1 in the first tapered portion 31 is larger than the gradient $((d22-d21)/L2)$ of the change in the diameter d2 in the second tapered portion 32. As shown in FIG. 3C, in the present embodiment, the boundary portion 36 is set at a position of, for example, 300 mm from the foremost distal end of the distal core portion 34.

In FIGS. 3B and 3C, the flexural load values and the diameters in the core wire of the contrast example are indicated by broken lines. In the contrast example, the length of the rigidity changing portion is, for example, 280 mm, and the start point of the proximal side of the rigidity changing portion is, for example, 300 mm from the foremost distal end.

As shown in FIG. 3C, in the contrast example, a range of the rigidity changing portion in the core wire is up to, for example, 300 mm from the foremost distal end of the core wire. On the other hand, in the present embodiment, by the first tapered portion 31 and the second tapered portion 32 in the guide wire rigidity changing portion 35, the range of the guide wire rigidity changing portion 35 in the core wire 20 is longer toward the proximal side than the contrast example, for example, the guide wire rigidity changing portion 35 extends beyond 300 mm from the foremost distal end of the core wire 20.

The gradient $((d12-d11)/L1)$ of the change in the diameter d1 in the first tapered portion 31 is larger than the gradient $((d22-d21)/L2)$ of the change in the diameter d2 in the second tapered portion 32. From this, as shown in FIG. 3B, in a unit length in the axial direction, the decrease in the rigidity in the first tapered portion 31 is larger than the decrease in the rigidity in the second tapered portion 32. As a result, the range having a relatively small rigidity expands in the axial direction as much as possible.

Furthermore, the axial direction length of the guide wire rigidity changing portion 35 becomes longer without structural modification (change in diameter, material, or the like) of the distal core portion 34 and the third tapered portion 33 continuous with the proximal end of the distal core portion 34. The distal core portion 34 and the third tapered portion 33 constitute the distal part of the core wire 20, and are sites that greatly affect the flexibility and usability of the guide wire 10. Therefore, even if the axial direction length of the guide wire rigidity changing portion 35 is changed, an occurrence of discomfort in usability by the operator is relatively small.

As shown in FIG. 3C, the gradient $\Delta 3$ $(=(d32-d31)/L3)$ of the change in the diameter d3 in the third tapered portion 33 of the present embodiment is substantially the same as the gradient of the change in the diameter in the rigidity changing portion in the contrast example. In other words, the gradient $\Delta n$ $(=(dn2-dn1)/Ln)$ of the change in the diameter do in the n-th tapered portion is substantially the same with respect to the gradient $\Delta 0$ $(=(d0-d4)/(300-\text{axial direction}$ length of the distal core portion)) of the change in the diameter determined by the distal end diameter d0 of the main body portion and the proximal end diameter d4 of the distal core portion when the range of the rigidity changing portion is up to, for example, 300 mm from the foremost distal end of the distal core portion. The axial direction length of the distal core portion 34 is, for example, 20 mm, and the length of the rigidity changing portion of the contrast example is, for example, 280 mm as described above.

As shown in FIG. 3B, the third tapered portion 33 continuous with the proximal side of the distal core portion 34 has substantially the same change in the flexural load values along the axial direction as the core wire in which the range of rigidity changing portion is up to, for example, 300 mm from the foremost distal end of the distal core portion (core wire of the contrast example). As the change in the flexural load values along the axial direction greatly affects the flexibility and usability of the guide wire 10, as described above, even if the axial direction length of the rigidity changing portion 35 is changed, an occurrence of discomfort in usability by the operator is relatively small.

The ratio of the gradients $(\Delta n/\Delta 0)$ is not limited to approximately one, and can be freely set within a range that does not cause a sense of discomfort in the usability by the operator. From this point of view, it is preferable that the ratio of gradients $(\Delta n/\Delta 0)$ be, for example, $0.27 \leq \Delta n/\Delta 0 \leq 1.80$. If the ratio of the gradients $(\Delta n/\Delta 0)$ is less than, for example, 0.27, the change in the rigidity of the core wire 20 is relatively poor, so that an unintended deviation in the guide wire 10 position is likely to occur. If the ratio of the gradients $(\Delta n/\Delta 0)$ exceeds, for example, 1.80, the change in rigidity of the core wire 20 is too large, and the operability of the guide wire 10 can be reduced. Therefore, the above range is preferable.

The diameter d12 of the proximal side of the first tapered portion 31 is substantially the same as the diameter d0 of the main body portion 30 so that the boundary between the main body portion 30 and the first tapered portion 31 is a continuous surface. Similarly, the diameter d22 of the proximal side of the second tapered portion 32 is substantially the same as the diameter d11 of the distal side of the first tapered portion 31. The diameter d32 of the proximal side of the third tapered portion 33 is substantially the same as the diameter d21 of the distal side of the second tapered portion 32. The diameter d4 of the distal core portion 34 is substantially the same as the diameter d31 of the distal side of the third tapered portion 33.

In the present specification, "continuous surface" means that an outer surface of the core wire 20 is smooth to the extent that the guide wire 10 does not get caught on an inner wall of the body lumen or the catheter 60. For example, when the diameter d12 of the proximal side of the first tapered portion 31 and the diameter d0 of the main body portion 30 are not formed substantially the same, a slight level difference is generated at the boundary between the first tapered portion 31 and the main body portion 30. However, by a coating layer 50, the outer surface of the guide wire 10 may be a substantially smooth surface, and the guide wire 10 may not be caught by the inner wall of the body lumen or the like. In such a case, even if the core wire 20 has a slight level difference, the outer surface of the core wire 20 can be regarded as a "continuous surface".

In accordance with an exemplary embodiment, a tapered angle (inclination angle to the axial direction of a tapered shape) of the first tapered portion 31 is constant along the axial direction. The tapered angle of the second tapered portion 32 is constant along the axial direction. The tapered angle of the third tapered portion 33 is constant along the axial direction.

Note that the tapered angle of each tapered portion 31, 32, and 33 can be changed along the axial direction. For example, when viewed in a cross section along the axial direction, the tapered angle can be changed so that a central part, for example, of the tapered portion 31, 32, and 33, bulges outward in a convex shape rather than having a linear shape when the tapered angle is constant.

Any combination may be made, for example, in such a manner that the tapered angles of the first tapered portion 31 and the third tapered portion 33 are constant along the axial direction and the tapered angle of the second tapered portion 32 is changed along the axial direction.

In accordance with an exemplary embodiment, the core wire 20 is formed by performing a cutting process or a polishing process for a forming material. The respective regions of the main body portion 30, the first tapered portion 31, the second tapered portion 32, the third tapered portion 33, and the distal core portion 34 can be simultaneously formed. In accordance with an exemplary embodiment, respective regions may be formed separately and sequentially. The manufacture of the core wire 20 is not limited to the cutting process or the polishing process, and can be formed by an etching or a laser process.

When the tapered angle is made constant along the axial direction, each tapered portion 31, 32, and 33 can be formed relatively more easily as compared with a case where the tapered angle is changed along the axial direction.

One example of dimensional specifications of the main body portion 30, the first tapered portion 31, the second tapered portion 32, the third tapered portion 33, and the distal core portion 34 is as shown in Table 1 below.

TABLE 1

| Region | Diameter [mm] | Axial Length [mm] | Gradient of Change in Diameter (Diameter Variation/Length) |
|---|---|---|---|
| Distal core portion 34 | Diameter d4: 0.080 | L4 = 20 | — |
| Third tapered portion 33 | Distal side diameter d31 (= d4) Proximal side diameter d32: 0.210 | L3 = 100 | 0.0013 |
| Second tapered portion 32 | Distal side diameter d21 (= d32) Proximal side diameter d22: 0.275 | L2 = 180 | 0.000361 |
| First tapered portion 31 | Distal side diameter d11 (= d22) Proximal side diameter d12 (= d0) | L1 = 100 | 0.00125 |
| Main body portion 30 | Diameter d0: 0.400 | (Depending on product length) | — |

Referring to FIG. 3C and Table 1, the gradient ((d12−d11)/L1) of the change in the diameter d1 in the first tapered portion 31 is larger than the gradient ((d22−d21)/L2) of the change in the diameter d2 in the second tapered portion 32.

Regarding the diameters d1, d2, and d3 of the respective tapered portions 31, 32 and 33, any of the following (1) to (3) can be said.

(1) It is preferable that the diameter d11 of the distal side in the first tapered portion 31 is, for example, 45% to 75% of the diameter d0 of the main body portion 30. In the example of Table 1, 0.275/0.400≈0.688. If the diameter d11 is less than, for example, 45% of the diameter d0, the core wire 20 becomes too soft, and the operability of the guide wire 10 can be reduced. If the diameter d11 exceeds, for example, 75% of the diameter d0, the rigidity of the core wire 20 is too high, so that an unintended deviation in the guide wire 10 position is likely to occur when the fixed state of the guide wire 10 can be loosened. Therefore, the above range is preferable.

(2) It is preferable that the gradient ((d12−d11)/L1) of the change in the diameter d1 in the first tapered portion 31 is, for example, 3.4 times to 21.7 times the gradient ((d22−d21)/L2) of the change in the diameter d2 in the second tapered portion 32. In the example of Table 1, 0.00125/0.000361≈3.46. If the gradient of the change in the diameter d1 is less than, for example, 3.4 times the gradient of the change in the diameter d2, the change in the rigidity of the core wire 20 can be relatively poor, so that an unintended deviation in the guide wire 10 position is likely to occur. If the gradient of the change in the diameter d1 exceeds, for example, 21.7 times the gradient of the change in the diameter d2, the change in rigidity of the core wire 20 is relatively too large, and the operability of the guide wire 10 can be reduced. Therefore, the above range is preferable.

(3) It is preferable that the change (d12−d21) in diameter in the first tapered portion 31 and the second tapered portion 32 is, for example, 1.4 times to 7.1 times the change (d32−d31) in the diameter in the third tapered portion 33. In the example of Table 1, (0.400−0.210)/(0.210−0.080) 1.46. If the change in diameter in the first tapered portion 31 and the second tapered portion 32 is less than, for example, 1.4 times the change in diameter in the third tapered portion 33, the change in the rigidity of the core wire 20 can be relatively poor, so an unintended deviation in the guide wire 10 position is likely to occur. If the change in diameter in the first tapered portion 31 and the second tapered portion 32 exceeds, for example, 7.1 times the change in diameter in the third tapered portion 33, the rigidity change of the core wire 20 is too large, and the operability of the guide wire 10 can be reduced. Therefore, the above range is preferable.

The relationships of the above (1) to (3) based on the dimensional specifications of the respective regions are equivalent to the relationships based on the flexural load values. The flexural load value is obtained by a flexural load value measurement.

Figure 4:
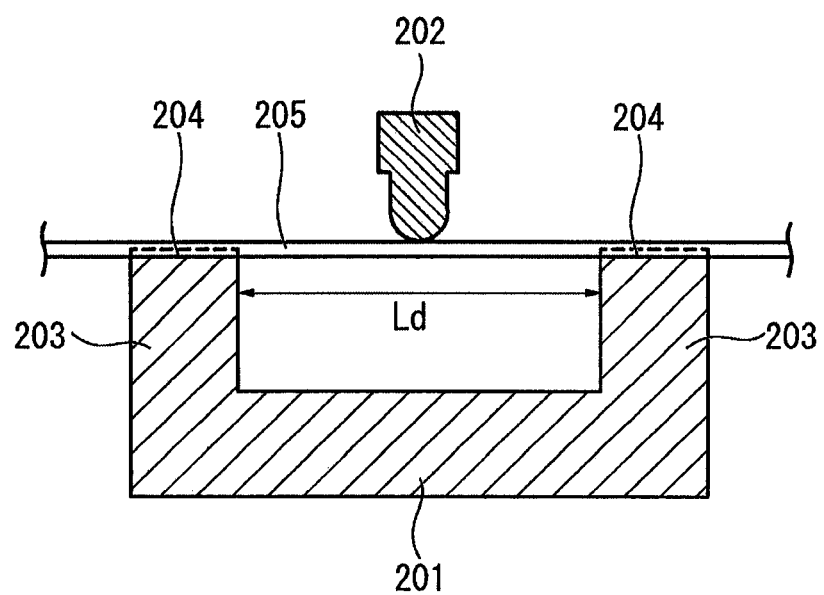
FIG. 4 is a cross-sectional diagram showing a schematic configuration of a measurement test device for measuring a flexural load value.

FIG. 4 is a cross-sectional diagram showing a schematic configuration of a measurement test device 200 for measuring the flexural load value.

Referring to FIG. 4, the measurement test device 200 has a fixing jig 201 for supporting an elongated measurement target object 205 and a pushing-down jig 202 disposed above the fixing jig 201. The fixing jig 201 has a pair of supporting legs 203 for supporting the measurement target object 205 at two points. The interval Ld between the supporting legs 203 is, for example, 25.4 mm. An upper surface of the supporting legs 203 is formed with a groove portion 204 into which the measurement target object 205 is fit. The pushing-down jig 202 is configured to be freely movable in an up-and-down manner with respect to the fixing jig 201. The pushing-down jig 202 is configured to freely adjust the speed at which the measurement target object 205 is pushed down and the dimension at which the measurement target object 205 is pushed down.

The measurement target objects 205 are the singleton of the core wire 20 of the guide wire 10, the singleton of the shaft portion 70 of the catheter 60, and the catheter assembly 100 in which the catheter 60 and the guide wire 10 are connected to each other.

In the present exemplary embodiment, using the measurement test device 200, a flexural load value measurement is performed under the following conditions to obtain a flexural load value. That is, the measurement target object 205 is supported at two points with, for example, a 25.4 mm gap. The pushing-down jig 202 moves at a speed, for example, of 5 mm/min. The supported central part of the measurement target object 205 is vertically pushed down by the pushing-down jig 202. The flexural load value is obtained by measuring the load when the measurement target object 205 is pushed down 2 mm, for example. Since it is necessary to support the measurement target object 205 at two points, the measurement of the flexural load value is started from a position, for example, 20 mm from the foremost distal end of the measurement target object 205. The measurement start position of the core wire 20 is a position of the distal end of the third tapered portion 33. In FIG. 3A the measurement values from a position 20 mm from the foremost distal end of each of the singleton core wire 20, the singleton shaft portion 70, and the catheter assembly 100 are plotted, and in FIG. 3B the measured values from the position of 20 mm from the foremost distal end of the singleton core wire 20 are plotted.

One example of the flexural load values of the main body portion 30, the first tapered portion 31, the second tapered portion 32, and the third tapered portion 33 of the core wire 20 is as shown in Table 2 below.

an unintended deviation in the guide wire 10 position is likely to occur. Therefore, the above range is preferable.

(5) Regarding the flexural load value obtained by the flexural load value measurement, it is preferable that a gradient ((f12−f11)/L1) of the change in the flexural load value f1 in the first tapered portion 31 is, for example, 5.3 times to 17.8 times the gradient ((f22−f21)/L2) of the change in the flexural load value f2 in the second tapered portion 32. In the example of Table 2, 0.55/0.10≈5.5. If the gradient of the change in the flexural load value f1 is less than, for example, 5.3 times the gradient of the change in the flexural load value f2, the change in the rigidity of the core wire 20 is relatively poor, so that an unintended deviation in the guide wire 10 position is likely to occur. If the gradient of the change in the flexural load value f1 exceeds, for example, 17.8 times the gradient of the change in the flexural load value f2, the change in rigidity of the core wire 20 is too large, and the operability of the guide wire 10 can be reduced. Therefore, the above range is preferable.

(6) Regarding the flexural load value obtained by the flexural load value measurement, it is preferable that the flexural load value f21 of the distal side in the second tapered portion 32 is, for example, 2.0 times to 22.3 times the flexural load value f31 near the distal end in the third tapered portion 33, and the flexural load value f12 of the proximal side in the first tapered portion 31 is, for example, 187 times to 239 times the flexural load value f31 near the distal end of the third tapered portion 33. In the example of Table 2, the former f21/f31 is 6.9/0.4=17.3 and the latter f12/f31 is 79.8/0.4≈199.5. If f21/f31 is less than, for example, 2.0 times, the change in the rigidity of the core wire 20 is relatively poor, so that an unintended deviation in the guide wire 10 position is likely to occur. If f21/f31 exceeds 22.3 times, the change in rigidity of the core wire 20 is too large, and the operability of the guide wire 10 is reduced. Further, if f12/f31 is less than, for example, 187 times, the rigidity of the distal core portion 34 is relatively high, and the risk of vascular damage can increase. If f12/f31 exceeds, for example, 239 times, the change in rigidity of the

TABLE 2

| Region | Flexural Load Value [gf] | Position from Distal End [mm] | Gradient of Change in Rigidity (Flexural Load Value Variation/Length) |
|---|---|---|---|
| Third tapered portion 33 | Flexural load value near distal end f31: 0.4 | 20 (Note 1) | 0.065 (Note 2) |
|  | Flexural load value of proximal side f32: 6.9 | 120 |  |
| Second tapered portion 32 | Flexural load value of distal side f21 (= f32) | 120 | 0.10 |
|  | Flexural load value of proximal side f22: 25.2 | 300 |  |
| First tapered portion 31 | Flexural load value of distal side f11 (= f22) | 300 | 0.55 |
|  | Flexural load value of proximal side f12 (= f0) | 400 |  |
| Main body portion 30 | Flexural load value f0: 79.8 | 400 | — |

(Note 1) It is a position of a distal end of a third tapered portion 33. A load value at this position is referred to as "flexural load value near distal end f31".
(Note 2) A length is, for example, 100 mm which is a measurable range.
Regarding the flexural load values f1, f2, and f3 of the respective tapered portions 31, 32 and 33, any of the following (4) to (6) can be said.

(4) Regarding the flexural load value obtained by the flexural load value measurement, it is preferable that a flexural load value f11 of the distal side in the first tapered portion 31 is, for example, 13% to 36% of a flexural load value f0 of the main body portion 30. In the example of Table 2, 25.2/79.8≈0.316. If the flexural load value f11 is less than, for example, 13% of the flexural load value f0, the core wire 20 becomes relatively too soft, and the operability of the guide wire 10 can be reduced. If the flexural load value f11 exceeds, for example, 36% of the flexural load value f0, the rigidity of the core wire 20 is too high, so that core wire 20 is too large, and the operability of the guide wire 10 can be reduced. Therefore, the above range is preferable.

In the present embodiment, the axial direction length of the core wire 20 has a length suitable for used in the TACE. In this case, the axial direction length L (L1+L2+L3) of the guide wire rigidity changing portion 35 (the first tapered portion 31, the second tapered portion 32, and the third tapered portion 33) is preferably, for example, 360 mm to 430 mm or 360 mm to 400 mm. By using the guide wire rigidity changing portion 35 of the length L, the region of the core wire 20 reaching the site from the aorta to the common hepatic artery (300 mm to 400 mm from the distal end) becomes relatively flexible, thereby the TACE can be suitably performed.

The boundary portion 36 between the first tapered portion 31 and the second tapered portion 32 is in a range of, for example, 200 mm to 400 mm from the distal end of the distal core portion 34, more preferably in a range of, for example, 250 mm to 350 mm from the distal end of the distal core portion 34, and still more preferably, the boundary portion 36 between the first tapered portion 31 and the second tapered portion 32, for example, is located in a range of, for example, 280 mm to 320 mm from the distal end of the distal core portion 34.

In accordance with an exemplary embodiment, the axial direction length L1 of the first tapered portion 31 is, for example, 80 mm to 230 mm, more preferably 80 mm to 170 mm, still more preferably 80 mm to 120 mm, and 100 mm is particularly preferable. By using the first tapered portion 31 of the axial direction length L1, the region of the core wire 20 reaching the site from the aorta to the common hepatic artery (for example, 300 mm to 400 mm from the distal end) becomes flexible, thereby the TACE can be suitably performed.

Further, in accordance with an exemplary embodiment, the axial direction length L2 of the second tapered portion 32 is, for example, 160 mm to 280 mm, more preferably 160 mm to 220 mm, still more preferably 160 mm to 200 mm, and 180 mm is particularly preferable. By using the second tapered portion 32 of the axial direction length L2, the region of the core wire 20 reaching the site from the common hepatic artery to the proper hepatic artery and further to the left and right hepatic artery (for example, 100 mm to 300 mm from the distal end) becomes relatively flexible, thereby the TACE can be suitably performed.

The position of the boundary portion 36 between the first tapered portion 31 and the second tapered portion 32 described above, the length of the first tapered portion 31, and the length of the second tapered portion 32 are based on sensory test results when the TACE is performed using a model that simulates the liver 90.

In the guide wire 10 of the present embodiment, the rigidity changes in the respective regions of the third tapered portion 33, the second tapered portion 32, and the first tapered portion 31. As shown to FIGS. 3A and 3B, the change in rigidity in the first tapered portion 31 is the largest (i.e., greatest). From this, in the present embodiment, the distal portion of the first tapered portion 31, in other words, between the second tapered portion 32 and the first tapered portion 31 is set as the guide wire rigidity changing point 37 (see reference numeral 37 in FIGS. 3A and 3B).

In accordance with an exemplary embodiment, with the guide wire rigidity changing point 37 as a boundary, the rigidity on the distal side is smaller than the rigidity on the proximal side, and the gradient of the change in the rigidity in the proximal side is larger than the gradient of the change in the rigidity in the distal side.

Action and Effect

In the catheter assembly 100, the distal side of the guide wire 10 is exposed from a distal end of the lumen 71 of the shaft portion 70, and the catheter hub 110 and the guide wire hub 120 are connected to each other in a state in which the guide wire rigidity changing point 37 that is set in the guide wire rigidity changing portion 35, and the catheter rigidity changing point 87 that is set in the catheter rigidity changing portion 85, are aligned with each other in the axial direction.

As shown in FIG. 3A, the rigidity on the proximal side of the catheter 60 (range indicated by reference numeral 81a in FIG. 3A) is larger than the rigidity on the distal side of the guide wire 10 (range indicated by reference numeral 33a in FIG. 3A). Assuming that the catheter having a rigidity larger than that of the distal side of the guide wire 10 and whose rigidity is constant in the axial direction is connected to the guide wire 10 having the guide wire rigidity changing portion 35, then the rigidity rapidly increases from the distal side to the proximal side at the boundary of the distal end of the catheter which is the starting point where the guide wire 10 is exposed. Therefore, despite the use of the guide wire 10 having flexibility, the flexibility can be lost and the operability of the integral structure type catheter assembly 100 can be impeded, which makes an occurrence of discomfort in usability by the operator.

On the other hand, in the present embodiment, when the guide wire 10 having the guide wire rigidity changing portion 35 is applied to the integral structure type catheter assembly 100, the catheter hub 110 and the guide wire hub 120 are connected to each other, in a state where the catheter 60 having the catheter rigidity changing portion 85 is combined, and further, the guide wire rigidity changing point 37 and the catheter rigidity changing point 87 are aligned with each other in an axial direction. According to such a configuration, by changing the rigidity of the catheter 60 in accordance with the rigidity change of the guide wire 10, it is possible to set the rigidity change in a desired pattern (i.e., desired stiffness) as a whole for the integral structure type catheter assembly 100. Therefore, according to the present embodiment, it is possible to provide an integral structure type catheter assembly 100 to which a guide wire 10 having a guide wire rigidity changing portion 35 is applied, which can suppress an occurrence of discomfort in usability and with improved operability.

As shown in FIG. 3A, the rigidity on the proximal side of the catheter 60 (range indicated by reference numeral 81a in FIG. 3A) is larger than the rigidity on the distal side of the catheter 60 (range indicated by reference numerals 82a and 83a in FIG. 3A). For this reason, the rigidity on the proximal side of the catheter assembly 100 can be increased as compared with a case where a catheter having a constant rigidity in the axial direction is applied. Therefore, a pushability of the catheter assembly 100 can be sufficiently transmitted to the distal end of the catheter assembly 100, and in turn, a pushability of the catheter assembly 100 can be sufficiently transmitted to the distal end of the guide wire 10. From this point of view, the operability of the catheter assembly 100 can be improved.

On the contrary, the rigidity on the distal side of the catheter 60 (range indicated by reference numeral 82a and 83a in FIG. 3A) is smaller as compared with the rigidity on the proximal side of the catheter 60 (range indicated by reference numerals 81a in FIG. 3A). Therefore, it is possible to minimize the change in flexibility of the distal side of the catheter assembly 100, and as a result, the change in rigidity from the distal side to the proximal side, where the distal end of the catheter at which the guide wire 10 is exposed is defined as a boundary, can be minimized. From this, the integral structure type catheter assembly 100 can be relatively smoothly bent and followed with respect to the branching or bending of blood vessels, and the operability of the catheter assembly 100 can be improved.

In accordance with an exemplary embodiment, the catheter 60 has a smaller rigidity on the distal side than the rigidity on the proximal side with the catheter rigidity changing point 87 as a boundary, and the material forming the proximal side of the shaft portion 70 and the material forming the distal side of the shaft portion 70 are different.

According to such a configuration, the rigidity of the catheter 60 can be changed in accordance with the rigidity change of the guide wire 10, and the rigidity change can be set in a desired pattern as a whole for the integral structure type catheter assembly 100.

In accordance with an exemplary embodiment, the guide wire 10 has a smaller rigidity on the distal side than the rigidity on the proximal side with the guide wire rigidity changing point 37 as a boundary, and the gradient of the change in the rigidity in the proximal side is larger than the gradient of the change in the rigidity in the distal side.

According to such a configuration, it is possible to obtain a large reduction in rigidity per unit length in the axial direction on the proximal side of the guide wire 10. As a result, the range having the relatively small rigidity (range having the flexibility) can be expanded as much as possible in the axial direction.

In accordance with an exemplary embodiment, each of the catheter 60 and the guide wire 10 has a length suitable for use in the TACE.

According to such a configuration, when performing the TACE, a region of the integral structure type catheter assembly 100 reaching the site from the aorta to the proper hepatic artery becomes relatively flexible, so that it is possible to suppress an occurrence of discomfort in usability and to improve the operability of the catheter assembly 100.

In the related art of the guide wire, the range in which the rigidity changing portion of the core wire is provided can be a range of, for example, at most 300 mm from a foremost distal end of the core wire. Therefore, in a case of the procedure in which a target site of treatment is present in the deep side of the body lumen, a large bending load acts on the core wire. The restoring force to return to the original straight state acts on the bent core wire. As a result, when a fixed state of the guide wire is loosened, a position of the guide wire is deviated in a direction to get out of the body. Thus, an unintended deviation in guide wire position can rather easily occur.

In order to reduce the unintended deviation in guide wire position, it is conceivable to widen a range in which the rigidity changing portion is provided in the core wire toward the proximal side. However, merely widening the range of the rigidity changing portion can cause a sense of discomfort in usability by an operator.

In the present embodiment, a guide wire 10 is provided that is capable of reducing an unintended deviation in a guide wire 10 position while suppressing an occurrence of discomfort with respect to usability.

Specifically, in accordance with an exemplary embodiment, the core wire 20 in the guide wire 10 arranges the boundary portion 36 between the first tapered portion 31 and the second tapered portion 32 in a range of, for example, 300 mm to 400 mm from the foremost distal end of the distal core portion 34, and sets a gradient d1 ((d12−d11)/L1) of the change in the diameter d1 in the first tapered portion 31 larger than a gradient ((d22−d21)/L2) of the change in the diameter d2 in the second tapered portion 32.

In this exemplary embodiment, by the first tapered portion 31 and the second tapered portion 32 in the guide wire rigidity changing portion 35, the range of the guide wire rigidity changing portion 35 in the core wire 20 is longer toward the proximal side beyond, for example, 300 mm from the foremost distal end of the core wire 20. The gradient ((d12−d11)/L1) of the change in the diameter d1 in the first tapered portion 31 is larger than the gradient ((d22−d21)/L2) of the change in the diameter d2 in the second tapered portion 32. Therefore, in a unit length in the axial direction, the decrease in the rigidity in the first tapered portion 31 is larger than the decrease in the rigidity in the second tapered portion 32. As a result, the range having a relatively small rigidity expands in the axial direction as much as possible. Therefore, as in TACE, even when the fixing state of the guide wire 10 is loosened in a case of performing a procedure in which the target site of treatment is present in the deep side of the body lumen, an unintended deviation in the guide wire 10 position can be reduced. Furthermore, the axial direction length of the guide wire rigidity changing portion 35 becomes longer without structural modification of the distal core portion 34 and the third tapered portion 33 continuous with the proximal end of the distal core portion 34. In accordance with an exemplary embodiment, the distal core portion 34 and the third tapered portion 33 constitute the distal part of the core wire 20, and are sites that greatly affect the flexibility and usability of the guide wire 10. Therefore, according to the present embodiment, it is possible to provide a guide wire 10 capable of reducing an unintended deviation in a guide wire 10 position while suppressing an occurrence of discomfort with respect to usability.

Hereinafter, with regard to the guide wire 10 of the present embodiment, other characteristic technical matters will be additionally described.

(1) The gradient $\Delta 3$ $(=(d32-d31)/L3)$ of the change in the diameter d3 in the third tapered portion 33 is $0.35 \leq \Delta n / \Delta 0 \leq 2.11$ with respect to the gradient $\Delta 0$ $(=(d0-d4)/(300-$axial direction length of the distal core portion)) of the change in the diameter determined by the distal end diameter d0 of the main body portion and the proximal end diameter d4 of the distal core portion when the range of the rigidity changing portion is up to, for example, 300 mm from the foremost distal end of the distal core portion.

In accordance with an exemplary embodiment, the change in the flexural load value along the axial direction can greatly affect the flexibility and usability of the guide wire 10. With such a configuration, even when the length of the rigidity changing portion 35 is set to a length exceeding, for example, 300 mm, the change in the flexural load value along the axial direction in the vicinity of the distal end (distal core portion 34 and third tapered portion 33) is substantially the same as when the length of the rigidity changing portion is, for example, 300 mm. For this reason, compared with the time of using the guide wire whose length of the rigidity changing portion is, for example, 300 mm, discomfort does not occur in usability. Therefore, it is possible to provide a guide wire 10 capable of reducing an unintended deviation in a guide wire 10 position while preventing an occurrence of discomfort with respect to usability.

(2) Regarding the diameter of each tapered portion, by satisfying any of the following conditions (a) to (c), it is possible to reduce an unintended deviation in the guide wire 10 position while preventing an occurrence of discomfort in usability.

(a) The diameter d11 of the distal side in the first tapered portion 31 is, for example, 45% to 75% of the diameter d0 of the main body portion 30.

(b) The gradient d1 ((d12−d11)/L1) of the change in the diameter d1 in the first tapered portion 31 is, for example, 3.4 times to 21.7 times the gradient ((d22−d21)/L2) of the change in the diameter d2 in the second tapered portion 32.

(c) The change (d12−d21) in diameter in the first tapered portion 31 and the second tapered portion 32 is, for example, 1.4 times to 7.1 times the change (d32−d31) in the diameter in the third tapered portion 33.

(3) The relationships among the above (a) to (c) are equivalent to the relationships based on the flexural load values. Therefore, regarding the flexural load values, by satisfying any of the following conditions (d) to (f), it is possible to reduce an unintended deviation in the guide wire 10 position while preventing an occurrence of discomfort in usability.

(d) Regarding the flexural load value obtained by the flexural load value measurement, the flexural load value f11 of the distal side in the first tapered portion 31 is, for example, 13% to 36% of the flexural load value f0 of the main body portion 30.

(e) Regarding the flexural load value obtained by the flexural load value measurement, the gradient ((f12−f11)/L1) of the change in the flexural load value f1 in the first tapered portion 31 is, for example, 5.3 times to 17.8 times the gradient ((f22−f21)/L2) of the change in the flexural load value f2 in the second tapered portion 32.

(f) Regarding the flexural load value obtained by the flexural load value measurement, the flexural load value f21 of the distal side in the second tapered portion 32 is, for example, 1.6 times to 14.9 times the flexural load value f31 near the distal end in the third tapered portion 33, and the flexural load value f12 of the proximal side in the first tapered portion 31 is, for example, 128 times to 239 times the flexural load value f31 near the distal end of the third tapered portion 33.

(4) The core wire 20 is formed of a single material.

With this configuration, the core wire 20 can be rather easily manufactured as compared with a case where the distal core portion 34, the guide wire rigidity changing portion 35, and the main body portion 30 are formed of different materials and joined.

(5) The tapered angle of the first tapered portion 31 is constant along the axial direction.

With this configuration, the first tapered portion 31 can be rather easily formed as compared with a case where the tapered angle is changed along the axial direction.

(6) The tapered angle of the second tapered portion 32 is constant along the axial direction.

With this configuration, the second tapered portion 32 can be rather easily formed as compared with a case where the tapered angle is changed along the axial direction.

(7) The tapered angle of the third tapered portion 33 is constant along the axial direction.

With this configuration, the third tapered portion 33 can be easily formed as compared with a case where the tapered angle is changed along the axial direction.

(8) The core wire 20 has a length suitable for use in the TACE. The axial direction length L of the guide wire rigidity changing portion 35 is, for example, 360 mm to 430 mm.

With this configuration, when performing the TACE, the region of the core wire 20 reaching the site (for example, 300 mm to 400 mm from the distal end) from the aorta to the proper hepatic artery becomes flexible, thereby it is possible to reduce an unintended deviation in the guide wire 10 position while preventing an occurrence of discomfort in usability.

(9) When the axial direction length L of the guide wire rigidity changing portion 35 is set to, for example, 360 mm to 430 mm, the axial direction length L1 of the first tapered portion 31 is, for example, 80 mm to 230 mm.

By using the first tapered portion 31 with the axial direction length L1, the TACE can be more suitably performed.

(10) When the axial direction length L of the guide wire rigidity changing portion 35 is set to, for example, 360 mm to 430 mm, the axial direction length L2 of the second tapered portion 32 is, for example, 160 mm to 280 mm.

By using the second tapered portion 32 with the axial direction length L2, the TACE can be more suitably performed.

Although the catheter assembly 100 according to the present disclosure has been described through the embodiment, the present disclosure is not limited only to each configuration demonstrated in this specification, and it is possible to change suitably based on the statement of claims.

For example, although the catheter assembly 100 which set the guide wire rigidity changing points 37 and 87 to set to one place is demonstrated, it is not limited to this configuration. In accordance with an exemplary embodiment, for example, two or more guide wire rigidity changing points 37 may be set, and two or more catheter rigidity changing points 87 may be set. Then, the catheter hub 110 and the guide wire hub 120 may be connected to each other to constitute the catheter assembly 100 in a state where two or more guide wire rigidity changing points 37 and two or more catheter rigidity changing points 87 are aligned with each other in the axial direction.

Although the catheter assembly 100 used for the TACE has been mentioned as an example, the catheter assembly 100 of the present disclosure can be used in other procedures. Each of the catheter 60 and the guide wire 10 may have an appropriate length according to the applied procedure.

Regarding the guide wire 10, although the embodiment in which the guide wire rigidity changing portion 35 is configured with three regions (tapered portions) has been described (for example, n=3), the guide wire rigidity changing portion 35 may be configured with, for example, four or more regions (tapered portions).

Regarding the guide wire 10, although the embodiment has been described in which the rigidity is changed along the axial direction by forming the core wire 20 from a single material and changing the diameter along the axial direction (that is, making the guide wire with a tapered shape), the present disclosure is not limited to the case. By using different materials for each constituent material of the main body portion 30, the guide wire rigidity changing portion 35, and the distal core portion 34, the rigidity can be changed along the axial direction. The main body portion 30, the guide wire rigidity changing portion 35, and the distal core portion 34 which are using different constituent materials can be joined by an appropriate known method such as welding, deposition, or adhesion. Each portion of the core wire 20 may be formed by combining the use of different constituent materials and the forming in a tapered shape.

Regarding the catheter 60, although the embodiment has been described in which the rigidity is changed along the axial direction by changing the hardness of the outer layer 73 in the shaft portion 70 along the axial direction, the present disclosure is not limited in this case. While the shaft portion 70 is formed of the same material, the rigidity can be changed along the axial direction by changing the thickness of the material along the axial direction. For example, the outer layer 73 in the shaft portion 70 can have a plurality of regions having different thickness along the axial direction, and the thickness constituting each region can be decreased toward the distal side (i.e., flexibility increases towards the distal side). The rigidity of the catheter 60 can be changed by a combination of both the hardness and thickness of the material.

The detailed description above describes embodiments of a catheter assembly. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter assembly comprising:
a catheter having a shaft portion, the shaft portion having a lumen;
a catheter hub configured to be attached to a proximal portion of the catheter;
a guide wire integral with the catheter, the guide wire having a flexible core wire and configured to be inserted into the lumen of the shaft portion and advanced into a body lumen together with the catheter to a target site in a periphery of the body lumen;
a guide wire hub configured to be attached to a proximal portion of the guide wire and is freely detachably connected to the catheter hub;
the guide wire having a guide wire rigidity changing portion that decreases in rigidity from a proximal side toward a distal side;
the catheter having a catheter rigidity changing portion that decreases in rigidity from a proximal side toward a distal side;
the catheter hub and the guide wire hub are connected to each other in a state where the distal side of the guide wire is exposed from a distal end of the lumen of the shaft portion; and
wherein a guide wire rigidity changing point in the guide wire rigidity changing portion and a catheter rigidity changing point in the catheter rigidity changing portion are aligned with each other in an axial direction such that the connection of the guide wire hub and the catheter hub maintain the alignment of the guide wire rigidity changing point and the catheter rigidity changing point as the guidewire and the catheter are advanced together to the target site.

2. The catheter assembly according to claim 1, wherein a rigidity of the catheter on the distal side of the catheter is less than a rigidity on the proximal side of the catheter with the catheter rigidity changing point as a boundary.

3. The catheter assembly according to claim 2, wherein a material forming a proximal side of the shaft portion and a material forming a distal side of the shaft portion are different.

4. The catheter assembly according to claim 1, wherein a rigidity of the guide wire on the distal side of the guide wire is less than a rigidity on the proximal side of the guide wire with the guide wire rigidity changing point as a boundary, and a gradient of a change in a rigidity in the proximal side of the guide wire is greater than a gradient of a change in a rigidity in the distal side of the guide wire.

5. The catheter assembly according to claim 1, comprising:
each of the catheter and the guide wire having a length for use in a transarterial chemoembolization.

6. The catheter assembly according to claim 1, wherein the core wire comprises:
a distal core portion that includes a foremost distal end, the distal core portion being most flexible in an entire length of the core wire;
a main body portion that constitutes a portion more proximal than the distal core portion and has a constant diameter along an axial direction; and
the guide wire rigidity changing portion that constitutes a portion from a distal end of the main body portion to a proximal end of the distal core portion and decreases in rigidity from the main body portion toward the distal core portion, wherein the guide wire rigidity changing portion includes at least:
a first tapered portion that is continuous with the distal end of the main body portion and has a diameter decreasing from the main body portion toward the distal core portion;
a second tapered portion that is continuous with a distal end of the first tapered portion and has a diameter decreasing from the first tapered portion toward the distal core portion;
an n-th tapered portion that is continuous with the proximal end of the distal core portion and has a diameter decreasing from an (n−1)th tapered portion being continuous with the proximal side toward the distal core portion;
a boundary portion between the first tapered portion and the second tapered portion is positioned in a range of 300 mm to 400 mm from the foremost distal end of the distal core portion; and
a gradient of a change in the diameter in the first tapered portion is larger than a gradient of a change in the diameter in the second tapered portion.

7. The catheter assembly according to claim 6, wherein n is equal to or greater than 3.

8. The catheter assembly according to claim 1, wherein the guide wire has a marker portion disposed at the distal portion of the core wire and a coating layer coating the core wire.

9. The catheter assembly according to claim 1, wherein the guide wire rigidity changing point in the guide wire rigidity changing portion and the catheter rigidity changing point in the catheter rigidity changing portion are aligned with each other in the axial direction within a threshold value.

10. The catheter assembly according to claim 9, wherein the threshold value is 20 mm.

11. The catheter assembly according to claim 1, wherein the catheter rigidity changing portion comprises a plurality of materials with a different hardness arranged along the axial direction.

12. The catheter assembly according to claim 11, wherein the hardness of the different materials constituting each region of the catheter rigidity changing portion decreases toward the distal side of the shaft portion of the catheter.

13. The catheter assembly according to claim 1, wherein the catheter rigidity changing portion comprises a plurality of regions, each of the plurality of regions having different thickness of an outer layer in the shaft portion of the catheter along the axial direction.

14. The catheter assembly according to claim 1, wherein the catheter has two or more catheter rigidity changing points and the guide wire has two or more guide wire rigidity changing points, and each of the two or more catheter rigidity changing points and the two or more guide wire rigidity changing points are aligned with each other in the axial direction.

15. A catheter assembly comprising:
a catheter having a shaft portion, the shaft portion having a lumen;

a guide wire integral with the catheter, the guide wire having a flexible core wire and configured to be inserted into the lumen of the shaft portion and advanced into a body lumen together with the catheter to a target site in a periphery of the body lumen;

the guide wire having a guide wire rigidity changing portion that decreases in rigidity from a proximal side toward a distal side;

the catheter having a catheter rigidity changing portion that decreases in rigidity from a proximal side toward a distal side; and wherein a guide wire rigidity changing point in the guide wire rigidity changing portion and a catheter rigidity changing point in the catheter rigidity changing portion are aligned with each other in an axial direction such that the alignment of the guide wire rigidity changing point and the catheter rigidity changing point is maintained as the guide wire and the catheter are advanced together to the target site.

16. The catheter assembly according to claim 15, wherein,
a rigidity of the catheter on the distal side of the catheter is less than a rigidity on the proximal side of the catheter with the catheter rigidity changing point as a boundary; and
a rigidity of the guide wire on the distal side of the guide wire is less than a rigidity on the proximal side of the guide wire with the guide wire rigidity changing point as a boundary, and a gradient of a change in a rigidity in the proximal side of the guide wire is greater than a gradient of a change in a rigidity in the distal side of the guide wire.

17. The catheter assembly according to claim 16, further comprising:
a catheter hub configured to be attached to a proximal portion of the catheter;
a guide wire hub configured to be attached to a proximal portion of the guide wire and is freely detachably connected to the catheter hub; and
the catheter hub and the guide wire hub are connected to each other in a state where the distal side of the guide wire is exposed from a distal end of the lumen of the shaft portion.

18. The catheter assembly according to claim 15, wherein the core wire comprises:
a distal core portion that includes a foremost distal end;
a main body portion that constitutes a portion more proximal than the distal core portion and has a constant diameter along an axial direction; and
the guide wire rigidity changing portion that constitutes a portion from a distal and of the main body portion to a proximal end of the distal core portion and decreases in rigidity from the main body portion toward the distal core portion, wherein the guide wire rigidity changing portion includes at least:
a first tapered portion that is continuous with the distal end of the main body portion and has a diameter decreasing from the main body portion toward the distal core portion;
a second tapered portion that is continuous with a distal end of the first tapered portion and has a diameter decreasing from the first tapered portion toward the distal core portion;
an n-th tapered portion that is continuous with the proximal end of the distal core portion and has a diameter decreasing from an (n−1)th tapered portion being continuous with the proximal side toward the distal core portion;

a boundary portion between the first tapered portion and the second tapered portion is positioned in a range of 300 mm to 400 mm from the foremost distal end of the distal core portion; and
a gradient of a change in the diameter in the first tapered portion is larger than a gradient of a change in the diameter in the second tapered portion.

19. A catheter assembly comprising:
a catheter having a shaft portion, the shaft portion having a lumen and a length of 700 mm to 2000 mm;
a guide wire integral with the catheter, the guide wire having a flexible core wire and configured to be inserted into the lumen of the shaft portion and advanced into a body lumen together with the catheter to a target site in a periphery of the body lumen, the guide wire having a length of 500 mm to 4000 mm;
the guide wire having a guide wire rigidity changing portion that decreases in rigidity from a proximal side toward a distal side;
the catheter having a catheter rigidity changing portion that decreases in rigidity from a proximal side toward a distal side;
wherein a guide wire rigidity changing point in the guide wire rigidity changing portion and a catheter rigidity changing point in the catheter rigidity changing portion are aligned with each other in an axial direction such that the alignment of the guide wire rigidity changing point and the catheter rigidity changing point is maintained as the guide wire and the catheter are advanced together to the target site; and
the core wire comprising:
a distal core portion that includes a foremost distal end;
a main body portion that constitutes a portion more proximal than the distal core portion and has a constant diameter along an axial direction; and
the guide wire rigidity changing portion that constitutes a portion from a distal end of the main body portion to a proximal end of the distal core portion and decreases in rigidity from the main body portion toward the distal core portion, and wherein the guide wire rigidity changing portion includes at least:
a first tapered portion that is continuous with the distal end of the main body portion and has a diameter decreasing from the main body portion toward the distal core portion;
a second tapered portion that is continuous with a distal end of the first tapered portion and has a diameter decreasing from the first tapered portion toward the distal core portion;
an n-th tapered portion that is continuous with the proximal end of the distal core portion and has a diameter decreasing from an (n−1)th tapered portion being continuous with the proximal side toward the distal core portion; and
a gradient of a change in the diameter in the first tapered portion is larger than a gradient of a change in the diameter in the second tapered portion.

20. The catheter assembly according to claim 19, further comprising:
a catheter hub configured to be attached to a proximal portion of the catheter;
a guide wire hub configured to be attached to a proximal portion of the guide wire and is freely detachably connected to the catheter hub; and the catheter hub and the guide wire hub are connected to each other in a state where the distal side of the guide wire is exposed from a distal end of the lumen of the shaft portion.

* * * * *